(12) United States Patent
Ishihara et al.

(10) Patent No.: US 11,740,198 B2
(45) Date of Patent: Aug. 29, 2023

(54) FORMALDEHYDE DETECTING SENSOR AND SYSTEM USING THE SAME

(71) Applicant: NATIONAL INSTITUTE FOR MATERIALS SCIENCE, Tsukuba (JP)

(72) Inventors: Shinsuke Ishihara, Tsukuba (JP); Jan Labuta, Tsukuba (JP); Takashi Nakanishi, Tsukuba (JP)

(73) Assignee: NATIONAL INSTITUTE FOR MATERIALS SCIENCE, Tsukuba (JP)

( * ) Notice: Subject to any disclaimer, the term of this patent is extended or adjusted under 35 U.S.C. 154(b) by 494 days.

(21) Appl. No.: 16/644,843

(22) PCT Filed: Aug. 24, 2018

(86) PCT No.: PCT/JP2018/031385
§ 371 (c)(1),
(2) Date: Mar. 5, 2020

(87) PCT Pub. No.: WO2019/049693
PCT Pub. Date: Mar. 14, 2019

(65) Prior Publication Data
US 2021/0372958 A1 Dec. 2, 2021

(30) Foreign Application Priority Data
Sep. 8, 2017 (JP) .............................. JP2017-172699

(51) Int. Cl.
G01N 27/12 (2006.01)
G01N 33/00 (2006.01)
B82Y 30/00 (2011.01)

(52) U.S. Cl.
CPC ....... *G01N 27/127* (2013.01); *G01N 33/0047* (2013.01); *B82Y 30/00* (2013.01)

(58) Field of Classification Search
CPC ... B82Y 30/00; G01N 27/127; G01N 33/0047
See application file for complete search history.

(56) References Cited

U.S. PATENT DOCUMENTS

| 2010/0075431 | A1 | 3/2010 | Zhou et al. |
| 2013/0202489 | A1 | 8/2013 | Ong et al. |
| 2015/0308995 | A1 | 10/2015 | Chen |

FOREIGN PATENT DOCUMENTS

| CN | 101535798 A | 9/2009 |
| CN | 101571506 A | 11/2009 |

(Continued)

OTHER PUBLICATIONS

Xie et al, Multi-wall carbon nanotube gas sensors modified with amino-group to detect low concentration of formaldehyde, 2012, Sensors and Actuators B: Chemical, vol. 168, pp. 34-38 (Year: 2012).*

(Continued)

*Primary Examiner* — Matthew D Krcha
*Assistant Examiner* — Austin Q Le
(74) *Attorney, Agent, or Firm* — Saliwanchik, Lloyd & Eisenschenk

(57) ABSTRACT

[Object] To provide a formaldehyde detecting sensor capable of constantly monitoring formaldehyde selectively and with high accuracy.
[Solving Means] A formaldehyde detecting sensor according to the present invention includes: a reaction portion that contains at least a hydroxylamine salt and reacts with formaldehyde to generate an acid; and a response unit that includes an electrode carrying a carbon material, an electrical resistance value of the carbon material varying depending on the acid generated in the reaction portion, in which the hydroxylamine salt and the carbon material are separated from each other.

14 Claims, 18 Drawing Sheets

(56) References Cited

FOREIGN PATENT DOCUMENTS

| CN | 103969252 A | | 8/2014 |
|---|---|---|---|
| CN | 106290488 A | | 1/2017 |
| JP | 2003-287500 A | | 10/2003 |
| JP | 2006047136 A | * | 2/2006 |
| JP | 2012-504227 A | | 2/2012 |
| JP | 2005-315739 A | | 11/2015 |
| JP | 2017-509859 A | | 4/2017 |
| WO | WO-2010/034840 A1 | | 4/2010 |
| WO | WO-2015/112213 A2 | | 7/2015 |

OTHER PUBLICATIONS

Li et al, n-Type gas sensing characteristics of chemically modified multi-walled carbon nanotubes and PMMA composite, 2007, vol. 121, issue 2, pp. 496-500 (Year: 2007).*

Office Action dated Jan. 19, 2022 in Chinese Application No. 201880057881.7.

International Search Report in International Aopiication No. PCT/JP2018/031385, filed Aug. 24. 2018.

Tang, X. et al., "Defect-free functionalized graphene sensor for formaldehyde detection," *Nanotechnology*, 2017, 28:1-11, 2016 IOP Publishing Ltd.

Tomčik, P. et al., "Microanalytical Determination of Formaldehyde by Direct Titration with Hydroxylamine Using Interdigitated Microelectrode Array Biamperometric End-Point Indicator," *Microchimica Acta*, 2003, 141:69-72, Springer-Verlag.

Shi, D. et al., "Solid organic acid tetrafluorohydroquinone functionalized single-walled carbon nanotube chemiresistive sensors for highly sensitive and selective formaldehyde detection," *Sensors and Actuators B: Chemical*, 2013, 177:370-375, 2012 Elsevier B.V.

\* cited by examiner

FORMALDEHYDE DETECTING SENSOR AND SYSTEM USING THE SAME

CROSS-REFERENCE TO RELATED APPLICATIONS

This application is the U.S. national stage application of International Patent Application No. PCT/JP2018/031385, filed Aug. 24, 2018, which claims the benefit under 35 U.S.C. § 119 of Japanese Application No. 2017-172699, filed Sep. 8, 2017, the disclosures of each of which are incorporated herein by reference in their entirety.

TECHNICAL FIELD

The present invention relates to a formaldehyde detecting sensor utilizing a change in an electrical resistance value, and a system using the same.

BACKGROUND ART

Formaldehyde is one of volatile organic compounds (VOCs), and is known to be harmful to the human body if it exceeds a certain amount. Formaldehyde is contained in, for example, a plywood, a lacquer, a building material, or the like, and is released into the atmosphere indoors, which can cause diseases such as sick house syndrome and cancer. In accordance with the World Health Organization (WHO), the standard for indoor formaldehyde concentration is 0.08 ppm or less.

As a method of easily detecting such formaldehyde, a detection tube is known (see, for example, Patent Literature 1). In accordance with Patent Literature 1, the detection tube is filed with a filler utilizing a reaction between hydroxylamine phosphate and formaldehyde, and is configured such that the filler changes color by the reaction. However, such a detection tube can detect formaldehyde at a desired place, but cannot constantly monitor formaldehyde and is disposable.

Meanwhile, it is known that a carbon nanotube exhibits semiconductivity at room temperature, and the electrical resistance value of the carbon nanotube easily changes when a gas or the like is adsorbed on the surface thereof. A sensor using such a carbon nanotube has been developed (see, for example, Patent Literatures 2 and 3). In accordance with Patent Literature 2, a sensor in which a carbon nanotube is positioned on an electrode is disclosed, a group that reacts with a compound to be detected being grafted in the carbon nanotube. A compound such as a volatile organic compound is detected using the change in the electrical resistance value of the carbon nanotube. In accordance with Patent Literature 3, a carbon nanotube is mounted on a radio frequency identification tag, and a volatile organic compound or the like is detected using the change in resistivity. However, neither of Patent Literatures 2 and 3 is selective for formaldehyde alone.

Another formaldehyde detecting sensor using a carbon nanotube has been developed (see, for example, Non-Patent Literature 1). Non-Patent Literature 1 reports that a carbon nanotube is functionalized with tetrafluorohydroquinone (TFQ), which improves conductivity by 20% with respect to 0.15 ppm of formaldehyde in dry air and provides high selectivity for formaldehyde. However, when the relative humidity is 20% or more, the sensitivity is greatly reduced, and thus, this formaldehyde detecting sensor is not suitable for use in a normal room.

Therefore, it is desired to develop a formaldehyde detecting sensor that exhibits high sensitivity to formaldehyde, has excellent selectivity, and is capable of constantly performing monitoring.

CITATION LIST

Patent Literature

Patent Literature 1: Japanese Patent Application Laid-open No. 2003-287500

Patent Literature 2: Japanese Patent Application Laid-open No. 2012-504227

Patent Literature 3: Japanese Unexamined Patent Application Publication No. 2017-509859

Non-Patent Literature

Non-Patent Literature 1: Shi et al., Sens. Actuator B-Chem., 2013, 177, 370-375

DISCLOSURE OF INVENTION

Technical Problem

In view of the above, it is an object of the present invention to provide a formaldehyde detecting sensor capable of constantly monitoring formaldehyde selectively and with high accuracy.

Solution to Problem

A formaldehyde detecting sensor according to the present invention includes: a reaction portion that contains at least a hydroxylamine salt and reacts with formaldehyde to generate an acid; and a response unit that includes an electrode carrying a carbon material, an electrical resistance value of the carbon material varying depending on the acid generated in the reaction portion, in which the hydroxylamine salt and the carbon material are separated from each other. This achieves the above-mentioned object.

The hydroxylamine salt may be a neutralized salt selected from the group consisting of a halide, a nitrate, a sulfate, a phosphate, a borate, and a trifluoroacetate of hydroxylamine ($NH_2OH$).

The hydroxylamine salt may be a neutralized salt selected from the group consisting of a halide, a nitrate, a sulfate, a phosphate, a borate, and a trifluoroacetate of $NH_2OR$ (R is an aromatic, cyclic, or acyclic hydrocarbon compound or a derivative thereof).

The carbon material may be selected from the group consisting of a carbon nanotube, a carbon nanohorn, graphene, fullerene, and derivatives thereof.

The carbon nanotube may contain 10 weight % or more of a semiconductor type carbon nanotube.

The carbon nanotube may contain 60 weight % or more of the semiconductor type carbon nanotube.

The carbon material may be coated with a dispersant selected from the group consisting of π-conjugated small molecule, a surfactant, a polymer, and a supramolecular polymer.

The supramolecular polymer may be represented by the following formula

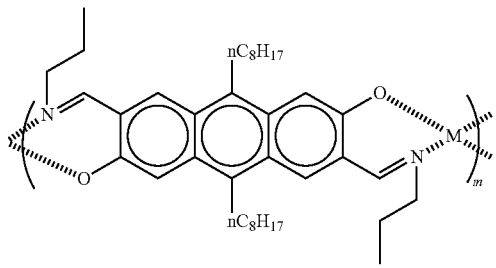

(Chem. 1)

where n represents linear $C_8H_{17}$, m is an integer of 2 to 200, M is a divalent transition metal selected from the group consisting of Cu, Ni, Pd, and Pt.

The hydroxylamine salt may be carried on a porous material.

The porous material may be selected from the group consisting of paper, a hydrophobic polymer, a hydrophilic polymer, porous glass, a porous carbon material, and porous oxide.

The formaldehyde detecting sensor may further include a spacer between the reaction portion and the response unit.

The hydroxylamine salt may be modified by a particle having a particle diameter in a range of 0.05 μm or more and 5000 μm or less.

The particle may be formed of a material selected from the group consisting of polystyrene (PS), polymethyl methacrylate (PMMA), polyacrylamide (PAM), polyethylene terephthalate (PET), polycaprolactone, polyvinyl acetate, polyvinyl ethyl acetate, carbon, glass, and silica.

The reaction portion may further contain a salt of a volatile acid selected from the group consisting of salts of hydrochloric acid, nitric acid, carbonic acid, perchloric acid, and trifluoroacetic acid.

A formaldehyde detecting system according to the present invention includes: a formaldehyde detecting sensor; and a detection means, in which the formaldehyde detecting sensor is the formaldehyde detecting sensor according to any one of claims 1 to 14, and the detection means detects a change in an electrical resistance value from the formaldehyde detecting sensor. This achieves the above-mentioned object.

The formaldehyde detecting sensor may be connected to a power source, and the detection means may be an ammeter or a light-emitting device.

The light-emitting device may be a light emitting diode.

The formaldehyde detecting system may further include a formaldehyde non-detection sensor that includes an electrode carrying a carbon material, in which the formaldehyde non-detection sensor is positioned so that the acid generated in the reaction portion is not supplied thereto.

The detection means may compare a change in an electrical resistance value from the formaldehyde detecting sensor and a change in an electrical resistance value from the formaldehyde non-detection sensor with each other to distinguish a response by formaldehyde and another response.

The formaldehyde detecting system may further include an airflow unit that causes air to flow to the carbon material of the response unit in the formaldehyde detecting sensor to remove the acid adsorbed on the carbon material.

Advantageous Effects of Invention

A formaldehyde detecting sensor according to the present invention is capable of detecting an acid generated in a reaction portion by using a change in an electrical resistance value of a carbon material of a response unit. In particular, by employing a hydroxylamine salt for the reaction portion, the hydroxylamine salt can be caused to selectively react with formaldehyde to generate an acid. Therefore, the sensor according to the present invention is capable of selectively detecting formaldehyde. Further, the carbon material is capable of detecting 0.05 ppm of formaldehyde as an actual measurement value at room temperature in air, and detecting 0.016 ppm of formaldehyde in theory, which makes it possible to perform detection with extremely high accuracy. The sensor according to the present invention can be repeatedly used by simply removing the acid adsorbed on the carbon material by a flow of air or the like. By combining the sensor according to the present invention with various detection devices, it is possible to provide a formaldehyde detecting system.

MODE(S) FOR CARRYING OUT THE INVENTION

Figure 1:
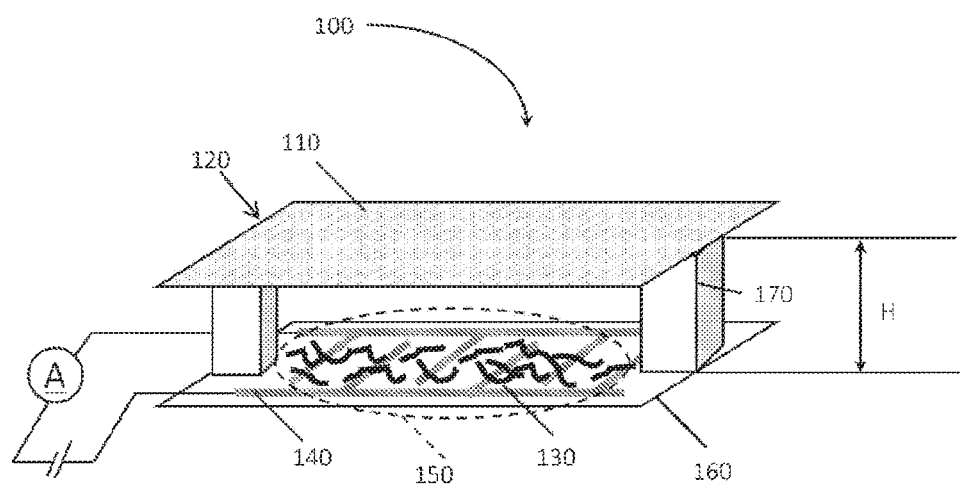
FIG. 1 is a schematic diagram showing an exemplary formaldehyde detecting sensor according to the present invention.

Hereinafter, embodiments of the present invention will be described with reference to the drawings. Note that similar components will be denoted by similar reference numerals, and description thereof will be omitted.

Embodiment 1

In an embodiment 1, a formaldehyde detecting sensor according to the present invention will be described.

FIG. 1 is a schematic diagram showing an exemplary formaldehyde detecting sensor according to the present invention.

A formaldehyde detecting sensor 100 (hereinafter, referred to simply as "sensor according to the present invention" in some cases) according to the present invention includes a reaction portion 120 and a response unit 150. The reaction portion 120 contains at least a hydroxylamine salt 110 and reacts with formaldehyde to generate an acid, the hydroxylamine salt 110 reacting with formaldehyde to be detected. The response unit 150 includes an electrode 140 carrying a carbon material 130, an electrical resistance value of the carbon material 130 varying depending on the acid generated in the reaction portion 120. Further, the sensor 100 according to the present invention is characterized by that the hydroxylamine salt 110 and the carbon material 130 are separated from each other. Note that in FIG. 1, the hydroxylamine salt 110 is schematically shown by dots for easy understanding.

The present inventors have utilized the fact that formaldehyde reacts with hydroxylamine phosphate as shown in Patent Literature 1, and focused on that the acid generated by the reaction causes the electrical resistance value of a carbon nanotube to change and functions as a sensor for detecting formaldehyde. However, the present inventors have found that the acid does not function as a sensor because a phenomenon in which the electric resistance reversibly changes in response to formaldehyde does not occur with favorable reproducibility although a change in the electrical resistance value is observed in the case where the hydroxylamine salt 110 such as hydroxylamine phosphate and the carbon material 130 such as a carbon nanotube are in contact with each other as shown in Comparative Example 3 described below, and that a change in the electrical resistance value occurs only in the case where the hydroxylamine salt 110 and the carbon material 130 are separated from each other, whereby the acid functions as a sensor. In the present specification, the phrase "separated from each other" means a state of not being in physical contact. Although the distance of "separated from each other" is not particularly limited as long as the acid generated in the reaction portion 120 is introduced into the response unit 150, the distance is, for example, 0.05 μm or more and 5000 μm or less.

Now, the operation principle of the sensor 100 according to the present invention will be described. When formaldehyde to be detected is introduced into the sensor 100 according to the present invention, the hydroxylamine salt 110 and formaldehyde react with each other in accordance with the following formula in the reaction portion 120, and volatile hydrochloric acid is generated as an acid. Although a case of hydroxylamine hydrochloride described below will be described here as the hydroxylamine salt 110 for the sake of simplicity, any hydroxylamine salt 110 generates an acid by a similar reaction.

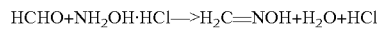

$HCHO + NH_2OH \cdot HCl \rightarrow H_2C=NOH + H_2O + HCl$

Subsequently, the generated hydrochloric acid is immediately diffused into the response unit 150 and adsorbed on the carbon material 130. The electric conductivity of the carbon material 130 increases by the adsorption of the acid. In such a change in the electric conductivity occurs, the presence of formaldehyde can be detected. In the present invention, the hydroxylamine salt 110 used for the reaction portion 120 does not react with VOCs typified by methanol, ethanol, toluene, and tetrahydrofuran (THF) other than formaldehyde, so that only formaldehyde can be detected selectively and with high accuracy.

Note that there is a possibility that the hydroxylamine salt 110 reacts with an aldehyde other than formaldehyde or a ketone to generate an acid. However, in the case where the presence of formaldehyde is suggested by the present sensor, the presence of formaldehyde can be determined by performing another precise analysis method (e.g., a coloration method based on lutidine formation or gas chromatography) that is not interfered by aldehydes other than formaldehyde and ketones. The sensor according to the present invention is capable of promptly notifying the necessity of inspection by a precise analysis method, by constantly monitoring formaldehyde.

The hydroxylamine salt 110 is a neutralized salt of an inorganic compound selected from the group consisting of a halide, a nitrate, a sulfate, a phosphate, a borate, and a trifluoroacetate of hydroxylamine ($NH_2OH$). These hydroxylamine salts 110 are readily available or can be synthesized. Among them, those that react with formaldehyde to generate a volatile acid (gas) are favorable, and examples thereof include halides ($NH_2OH \cdot HCl$, $NH_2OH \cdot HBr$, $NH_2OH \cdot HF$) and trifluoroacetates of hydroxylamine.

Alternatively, the hydroxylamine salt 110 is a neutralized salt of an organic compound selected from the group consisting of a halide, a nitrate, a sulfate, a phosphate, a borate, and a trifluoroacetate of $NH_2OR$ (R is an aromatic, cyclic, or acyclic hydrocarbon compound, or a derivative thereof). Among them, halides ($NH_2OR \cdot HCl$, $NH_2OR \cdot HBr$, $NH_2OR \cdot HF$) in which R is an aromatic benzene ring or nitrobenzene, trifluoroacetates, and the like are favorable.

The reaction portion 120 only needs to contain at least the hydroxylamine salt 110. However, in the case where a non-volatile acid (liquid) is generated by the reaction between the hydroxylamine salt 110 and formaldehyde, the non-volatile acid is not efficiently adsorbed on the carbon material 130 in some cases. Therefore, the reaction portion 120 may further contain, in addition to the hydroxylamine salt 110, a salt of a volatile acid selected from the group consisting of salts of hydrochloric acid, nitric acid, carbonic acid, perchloric acid, and trifluoroacetic acid. These salts of volatile acids react with a non-volatile acid to generate a volatile acid, so that the sensor 100 according to the present invention is capable of improving the ability to detect formaldehyde.

The carbon material 130 is not particularly limited as long as it is a material containing carbon whose electrical resistance value changes due to the adsorption of an acid. Examples of the carbon material 130 include a material selected from the group consisting of a carbon nanotube, a carbon nanohorn, graphene, fullerene, and derivatives thereof. It is known that the electrical resistance value thereof changes by the adsorption of an acid. Among them, the carbon nanotube is favorable because it is easily available. As the derivatives, those having a functional group such as an amine and a carboxylic acid on the surface thereof and those having a surface coated with a dispersant or the like are intended.

The carbon material 130 desirably overlaps while having a space so that an acid is easily adsorbed thereon, and can form a network structure (network).

Further, the carbon nanotube can be classified into a single-walled, double-walled, and multi-walled carbon nanotubes in accordance with the number of walls of graphene overlapping, and any of them can be employed in the present invention. Among them, a single-walled carbon nanotube (SWCNT) is favorable because it has high electric conductivity and has an electrical resistance value that easily changes due to an acid.

It is known that there are two types of carbon nanotubes, i.e., a semiconductor type one and a metal type one. In the case where a semiconductor type carbon nanotube is employed in the sensor 100 according to the present invention, the content of semiconductor type carbon nanotube is favorable 10 weight % or more because there is a possibility that a sufficient change in the electrical resistance value to an acid cannot be achieved in the case where the content is less than 10 weight %. More favorably, the content of the semiconductor type carbon nanotube is 60 weight % or more. This makes it possible to improve the sensitivity for detecting formaldehyde. Note that favorably, the content of the semiconductor type carbon nanotube is 90 weight % or more. In particular, the content of the semiconductor type single-walled carbon nanotube is favorably 10% or more, more favorably 60% or more, and still more favorably 90% or more.

Further, it is naturally favorable that the carbon nanotube is all constituted by the semiconductor type carbon nanotube. However, even in the case where the carbon nanotube contains a metal type carbon nanotube in the range of 5 weight % or more and less than 10 weight %, there is no problem in the accuracy of the sensor.

The carbon material 130 favorably has a large surface area so as to promote the adsorption of an acid. From this viewpoint, it is desirable to enhance the dispersibility of the carbon material 130, and it is favorable that the carbon material 130 is partially coated with a dispersant including a π-conjugated small molecule, a surfactant, a polymer, and a supramolecular polymer. It is known that these dispersants partially coat the above-mentioned carbon material 130 and enhances the dispersibility. In the case where the dispersibility of the carbon material 130 on an electrode increases, the surface area interacting with the acid increases, so that formaldehyde can be detected with high accuracy. Note that the amount of "partially" may be any amount as long as the carbon material 130 is not completely coated. For example, in the case where the carbon material 130 is a carbon nanotube, the amount of "partially" is in the range of 5% or more and 90% or less, favorably 10% or more and 50% or less of the surface area.

Examples of the π-conjugated small molecule include pyrene, anthracene, and porphyrin. The surfactant is used when the carbon material 130 is solubilized in a solvent. Examples of the surfactant include sodium dodecyl sulfate (SDS), sodium dodecylbenzene sulfate (SDBS), sodium cholate (SC), and sodium deoxycholate (DOC). It is known that also the polymer solubilizes the carbon material 130 in a solvent. Examples of such a polymer include a polysilane, a polythiophene, and a polyfluorene. As the supramolecular polymer, those having a monomer unit linked by a non-covalent bond are intended. Examples of the supramolecular polymer include a supramolecular polymer represented by the following formula. A technology for coating a carbon nanotube with such a supramolecular polymer is known, and improvement in dispersibility has been confirmed.

(Chem. 2)

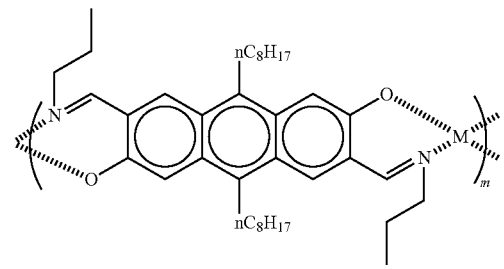

Here, n represents linear $C_8H_{17}$, m is a natural number of 2 to 200, and M represents a divalent transition metal ion selected from the group consisting of Cu, Ni, Pd, and Pt.

Note that the dispersant specifically specified here is merely an example, and is not particularly limited as long as the dispersibility can be improved.

The carbon material 130 is carried on the electrode 140 formed of a commonly used electrode material. The electrode 140 is formed of, for example, a material selected from the group consisting of Au, Pt, Ag, and alloys thereof, or a conductive carbon material such as glassy carbon. The shape of the electrode 140 differs depending on the method of detecting a change in the electrical resistance value, but examples thereof include a comb electrode (e.g., FIG. 1) and a interdigital electrode. Therefore, the electrode 140 is located on a substrate 160 in FIG. 1.

The hydroxylamine salt 110 may be carried on a porous material. This makes the handling of the reaction portion 120 simple, promotes the reaction between the hydroxylamine salt 110 and formaldehyde, and separates the hydroxylamine salt 110 and the carbon material 130 from each other more easily. Such a porous material may include a material that has no reactivity with the hydroxylamine salt 110 and has pores capable of carrying the hydroxylamine salt 110. Examples of the porous material include a material selected from the group consisting of paper typified by filter paper or the like, a hydrophobic polymer, a hydrophilic polymer, porous glass, a porous carbon material, and porous oxide. These are commercially available porous materials.

The hydrophobic polymer is, for example, polyvinylidene fluoride (PFVD) or polytetrafluoroethylene (PTFE), which is favorable because the hydroxylamine salt 110 can be easily carried and it has no reactivity with the hydroxylamine salt 110. Examples of the porous carbon material include replica of porous silica obtained using porous silica as a template. The porous oxide includes $TiO_2$, $CeO_2$, $ZrO_2$, ZnO, $SiO_2$, or the like, but may include a hollow body constituted by nanoparticles or a core-shell structure.

It is favorable that the porous material has a specific surface area in the range of 10 $m^2/g$ or more and 5000 $m^2/g$ or less, a pore diameter in the range of 10 nm or more and 100 μm or less, and a pore volume in the range of 0.05 $cm^3/g$ or more and 0.90 $cm^3/g$ or less. This makes it possible to carry the hydroxylamine salt 110 that is required for the reaction and does not need to be replaced in the future.

As shown in FIG. 1, in the sensor 100 according to the present invention, a spacer 170 may be located between the reaction portion 120 and the response unit 150 so that the hydroxylamine salt 110 and the carbon material 130 are separated from each other. The material of the spacer 170 is not particularly limited. A height H of the spacer 170 only needs to be in the above-mentioned range of 0.05 μm or more and 5000 μm or less.

Figure 2:
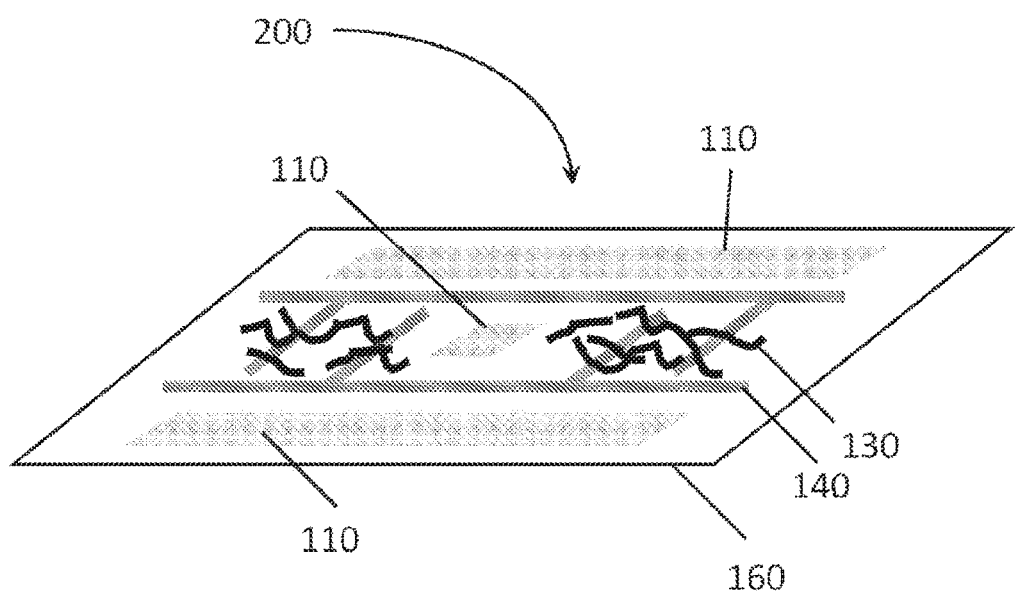
FIG. 2 is a schematic diagram showing another exemplary formaldehyde detecting sensor according to the present invention.

FIG. 2 is a schematic diagram showing another exemplary formaldehyde detecting sensor according to the present invention.

A sensor 200 in FIG. 2 is similar to the sensor 100 except that the spacer 170 is not provided, i.e., the method of separating the hydroxylamine salt 110 and the carbon material 130 from each other differs.

In detail, in the sensor 200 in FIG. 2, the hydroxylamine salt 110 is patterned near the electrode on which the carbon material 130 is carried. Such patterning can be performed by, for example, an inkjet printer or the like. Since the spacer 170 is not provided, the size and thickness of the sensor 200 can be reduced.

Figures 3A, 3B:
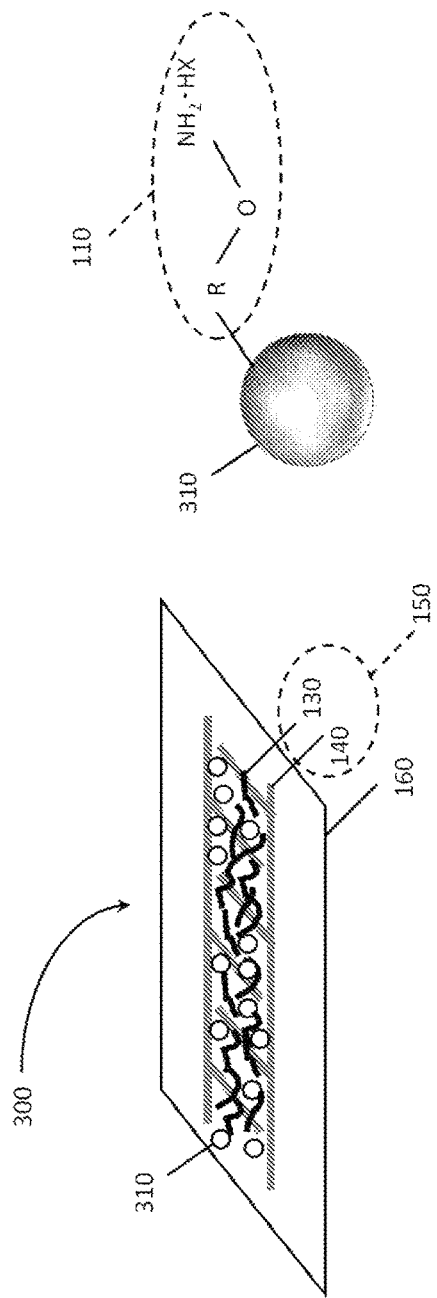
FIGS. 3A-3B are schematic diagrams showing still another exemplary formaldehyde detecting sensor according to the present invention.

FIGS. 3A-3B are schematic diagrams showing still another exemplary formaldehyde detecting sensor according to the present invention.

A sensor 300 in FIG. 3A is similar to the sensor 100 except that the spacer 170 is not provided, i.e., the method of separating the hydroxylamine salt 110 and the carbon material 130 from each other differs.

In detail, in the sensor 300 in FIGS. 3A-3B, the hydroxylamine salt 110 is modified into a particle 310 (FIG. 3B). In order for the hydroxylamine salt 110 and the carbon material 130 to be separated from each other, it is favorable that the particle diameter of the particle 310 is in the range of 0.05 μm or more and 5000 μm or less. In the case where the particle diameter is less than 0.05 μm, there is a possibility that the hydroxylamine salt 110 and the carbon material 130 come into contact with each other over a wide area and the reversibility of the electrical resistance value due to an acid is impaired. In the case where the particle diameter exceeds 5000 μm, the amount of the hydroxylamine salt 110 carried on the particle surface is reduced and the amount of a generated acid is reduced, so that there is a possibility that the sensitivity to formaldehyde is impaired. It is favorable that the particle diameter is in the range of 10 μm or more and 500 μm or less, more favorably 50 μm or more and 300 μm or less. Here, the particle diameter is a volume-based median diameter (d50), and can be measured by, for example, a microtrac method or a laser scattering method.

The particle 310 modified by the hydroxylamine salt 110 is formed of a material selected from the group consisting of polystyrene (PS), polymethyl methacrylate (PMMA), polyacrylamide (PAM), polyethylene terephthalate (PET), polycaprolactone, polyvinyl acetate, polyvinyl ethyl acetate, carbon, glass, and silica. All of these particles are easily available. Among them, PS, PMMA, and the like are favorable because they easily cause the hydroxylamine salt 110 to modify them.

In FIGS. 3A-3B, a case where the hydroxylamine salt 110 is a monovalent acid salt (X represents a monovalent base in FIGS. 3A-3B) is exemplarily shown. However, the hydroxylamine salt 110 modified into the particle 310 may be the same as the above-mentioned hydroxylamine salt 110. That is, the hydroxylamine salt 110 modified into the particle 310 is a neutralized salt of an organic compound selected from the group consisting of a halide, a nitrate, a sulfate, a phosphate, a borate, and a trifluoroacetate of $NH_2OR$ (R is an aromatic, cyclic, or acyclic hydrocarbon compound, or a derivative thereof).

Note that in the sensor 300 in FIGS. 3A-3B, a gas-permeable spacer (not shown) such as paper may be inserted between the response unit 150 and the particle 310 modified by the hydroxylamine salt 110 to surely inhibit the hydroxylamine salt 110 and the carbon material 130 from being in physical contact with each other.

Next, an exemplary process of producing the formaldehyde detecting sensor 100 according to the present invention will be described.

First, the substrate 160 including the electrode 140 is prepared. The carbon material 130 is dispersed in a solvent. The solvent is not particularly limited as long as it is volatile. Examples of the solvent include a mixed solvent of o-dichlorobenzene and toluene. Note that when the carbon material 130 is coated with a dispersion medium, the above-mentioned dispersion medium only needs to be added thereto. Subsequently, this suspension is drop-cast on the electrode 140. After the solvent is dried, the response unit 150 is obtained.

Subsequently, the hydroxylamine salt 110 is added to a solvent such as methanol, and this solution is drop-cast on or immersed in a porous material. By drying and removing the excess solvent, the reaction portion 120 is obtained. By providing the spacer 170 on the response unit 150, covering the spacer 170 with the reaction portion 120, and fixing them, the sensor 100 according to the present invention is obtained.

Next, an exemplary process of producing the formaldehyde detecting sensor 200 according to the present invention will be described.

Since the procedure of producing the response unit 150 is similar to that of the sensor 100, description thereof will be omitted. By masking a predetermined portion of the response unit 150 and printing the hydroxylamine salt 110 using an inkjet printer or the like, the sensor 200 according to the present invention is obtained.

Next, an exemplary process of producing the formaldehyde detecting sensor 300 according to the present invention will be described.

Since the procedure of producing the response unit 150 is similar to that of the sensor 100, description thereof will be omitted. Next, the particle 310 that modifies the hydroxylamine salt 110 is prepared. The particle 310 that modifies the hydroxylamine salt 110 can be easily obtained by treating the particle 310 modified by hydroxylamine or a derivative thereof in an acid. By positioning this on the carbon material 130 of the response unit 150, the sensor 300 according to the present invention is obtained. A gas-permeable spacer such as paper may be inserted between the particle 310 and the response unit 150.

Embodiment 2

In an embodiment 2, a system using the formaldehyde detecting sensor according to the present invention described in the embodiment 1 will be described.

Figure 4:
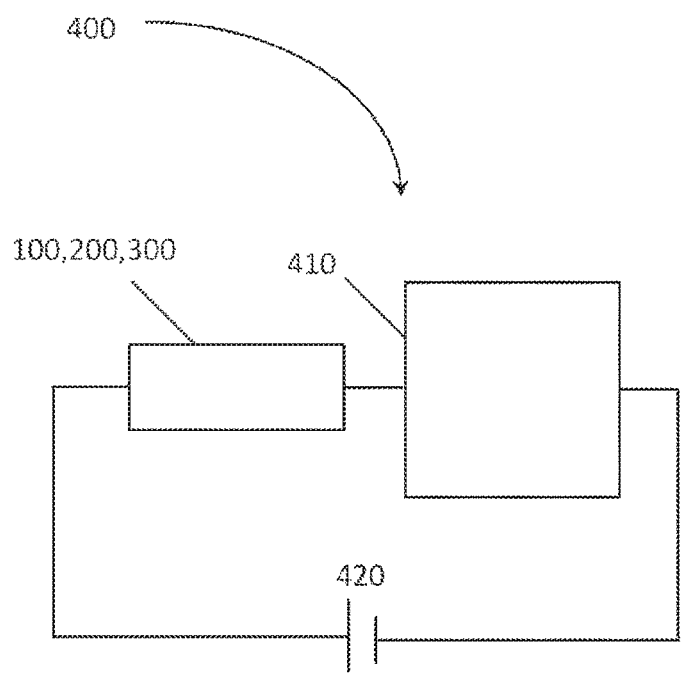
FIG. 4 is a schematic diagram showing a formaldehyde detecting system according to the present invention.

FIG. 4 is a schematic diagram showing a formaldehyde detecting system according to the present invention.

A formaldehyde detecting system 400 (hereinafter, referred to simply as "system according to the present invention" in some cases) according to the present invention includes the formaldehyde detecting sensor 100, 200, or 300 according to the present invention, and a detection means 410 that detects a change in the electrical resistance value from the sensor 100, 200, or 300. In FIG. 4, the system 400 according to the present invention is connected to a power source 420. The power source 420 may be a fixed power source or may be a battery or the like. By employing a battery as the power source 420, it is possible to provide a small portable system 400.

The detection means 410 is not particularly limited as long as it is capable of detecting a change in the electrical resistance value, but is, for example, an ammeter or a light-emitting device. In the case of an ammeter, when the voltage of the power source 420 is known, a change in the electrical resistance value can be detected by measuring the magnitude of a current. In the case of a light-emitting device, a change in the electrical resistance value can be detected by observing a change in the luminance. As such a light-emitting device, a light emitting diode can be used simply. By using a light emitting diode, a change in the luminance can be visually detected, so that it is possible to provide a portable and simple system 400. Alternatively, the detection means 410 may be a sound alarm. By setting the sound alarm so as to generate an audio when the electrical resistance value changes from a predetermined electrical resistance value, it is possible to detect formaldehyde by the audio.

Alternatively, the system 400 may include a control unit (not shown) in which data of an erroneous response based on temperature or humidity is stored in a database in advance, and the control unit may compare the change in the electrical resistance value of the carbon material 130 in the sensor 100, 200, or 300 according to the present invention detected by the detection means 410 and the data stored in the database of the control unit with each other to distinguish the correct response and the erroneous response from each other.

As described in the embodiment 1, the sensor 100, 200, or 300 according to the present invention detects formaldehyde by using a change in the electrical resistance value, which is caused by the acid generated in the reaction portion 120 being adsorbed on the carbon material 130 of the response unit 150. However, the system 400 according to the present invention may further include an airflow unit or a fan that causes air to flow to the carbon material 130 of the response unit 150. Accordingly, the acid adsorbed on the carbon material 130 is quickly removed, so that the sensor 100, 200, or 300 according to the present invention can be repeatedly used. Note that the air may be air, nitrogen, argon, or the like.

Figure 5:
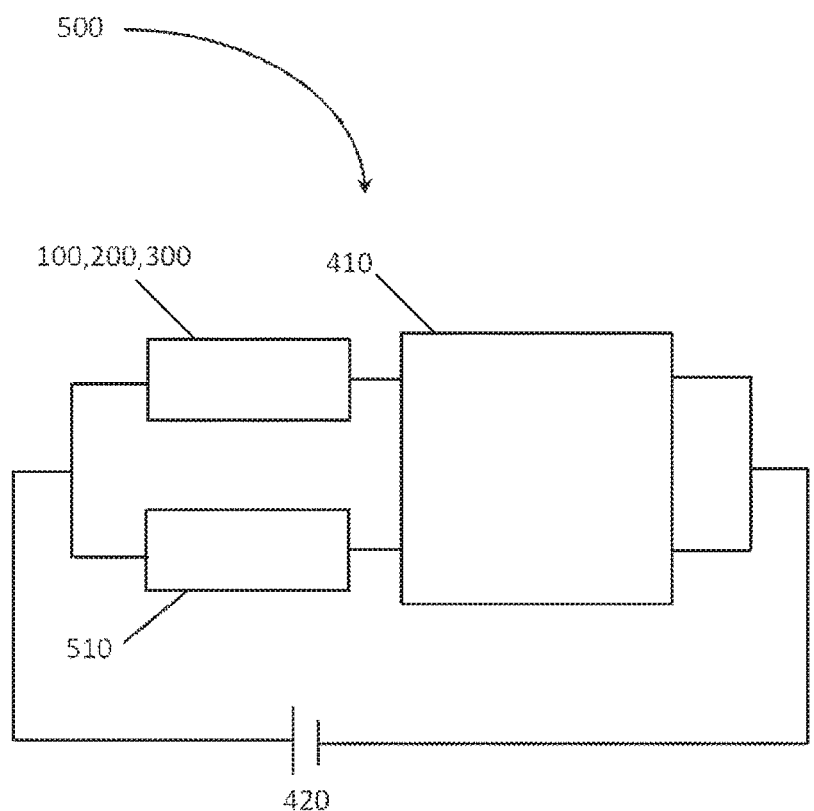
FIG. 5 is a schematic diagram showing another formaldehyde detecting system according to the present invention.

FIG. 5 is a schematic diagram showing another formaldehyde detecting system according to the present invention.

Another formaldehyde detecting system 500 according to the present invention is different from the system 400 in that it includes a formaldehyde non-detection sensor 510 (hereinafter, referred to simply as "non-detection sensor"). In FIG. 5, the non-detection sensor 510 includes an electrode on which the carbon material 130 is carried, and is positioned so that the acid generated in the reaction portion 120 of the sensor 100, 200, or 300 according to the present invention is not supplied thereto. For this reason, the non-detection sensor 510 does not respond to formaldehyde, but can respond to other environments such as temperature and humidity in a way similar to those of the sensor 100, 200, or 300.

The detection means 410 detects a change in the electrical resistance value (based on formaldehyde) of the carbon material 130 in the sensor 100, 200, or 300 according to the present invention and a change in the electrical resistance value (based on temperature or humidity) of the carbon material in the non-detection sensor 510 and compares them with each other, making it possible to distinguish the correct response and the erroneous response from each other. Also here, since the correct response and the erroneous response can be easily distinguished from each other by comparing the magnitude of the current value in the case where the detection means 410 is an ammeter, or by comparing the magnitude of the luminance in the case where the detection means 410 is a light-emitting device, it is possible to provide a system that detects only formaldehyde with high accuracy. Note that such a comparison may be visually performed or may be automatically performed by a control unit (not shown) provided separately, and displayed on a display unit (not shown).

In the system 500, the non-detection sensor 510 is configured to detect an erroneous response other than formaldehyde. However, as the non-detection sensor 510, a resistor having the same electrical resistance value as the electrical resistance value in the initial state of the sensor 100, 200, or 300 may be used. In this case, although it is difficult to distinguish the correct response and the erroneous response from each other, formaldehyde can be easily detected from, for example, a change in the current value or luminance from the detection means 410 connected to each of the sensor 100, 200, or 300 and the non-detection sensor 510.

Hereinafter, embodiments of the present invention will be described more specifically with reference to Examples and Comparative Example. However, the present invention is not limited to the scope of the Examples.

EXAMPLE

[Reagent and Material]

Reagents and materials used in the following Examples, Comparative Example, and Reference Example will be described. All reagents were special grade reagents, purchased from Sigma-Aldrich, Tokyo Chemical Industry Co., Ltd., and Alfa Aesar, and used as they were without purification. As hydroxylamine salts, three types represented by the following formulae were used.

(Chem. 3)

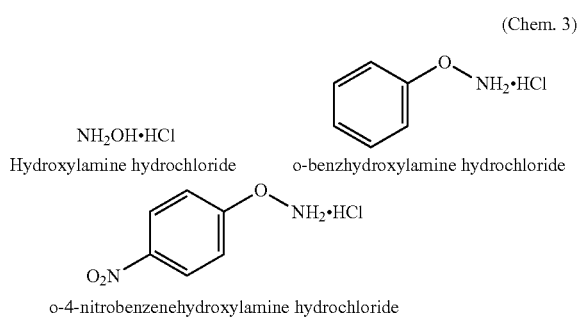

Single-walled carbon nanotubes (SWCNTs) prepared by a HiPco (high-pressure CO) method utilizing a heterogeneous reaction of carbon monoxide were purchased from NanoIntegris, USA. The SWCNTs were separated into a semiconductor type one and a metal type one on the basis of Yomogida, Y. et al., Nat. Commun., 2016, 7, 12056. A supramolecular polymer represented by the following formula was prepared on the basis of Ishihara, S. et al., J. Am. Chem. Soc., 2016, 138, 8221-8227. Also here, n represents linear $C_8H_{17}$ and the average value of m was approximately 15 to 20. As the electrode, a comb electrode (manufactured by BVI Technologies, No. CC1.W1) formed of Au on a ceramic substrate formed of aluminum oxide was used. The inter-electrode distance was 200 μm.

(Chem. 4)

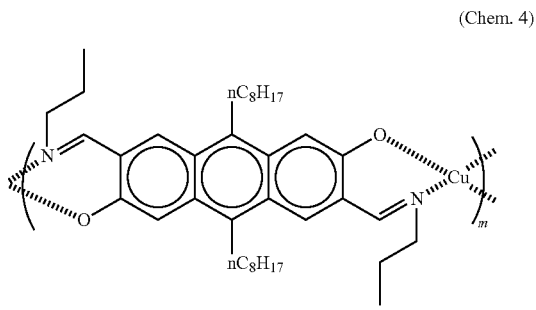

Example 1

In Example 1, the formaldehyde detecting sensor 100 shown in FIG. 1 in which $NH_2OH \cdot HCl$ (hydroxylamine hydrochloride) and SWCNTs (including 95 weight % of a semiconductor type one and 5 weight % of a metal type one) were respectively used as the hydroxylamine salt 110 and the carbon material 130 was produced, a PVDF membrane filter being caused to carry the hydroxylamine salt 110 in the formaldehyde detecting sensor.

Figure 6:
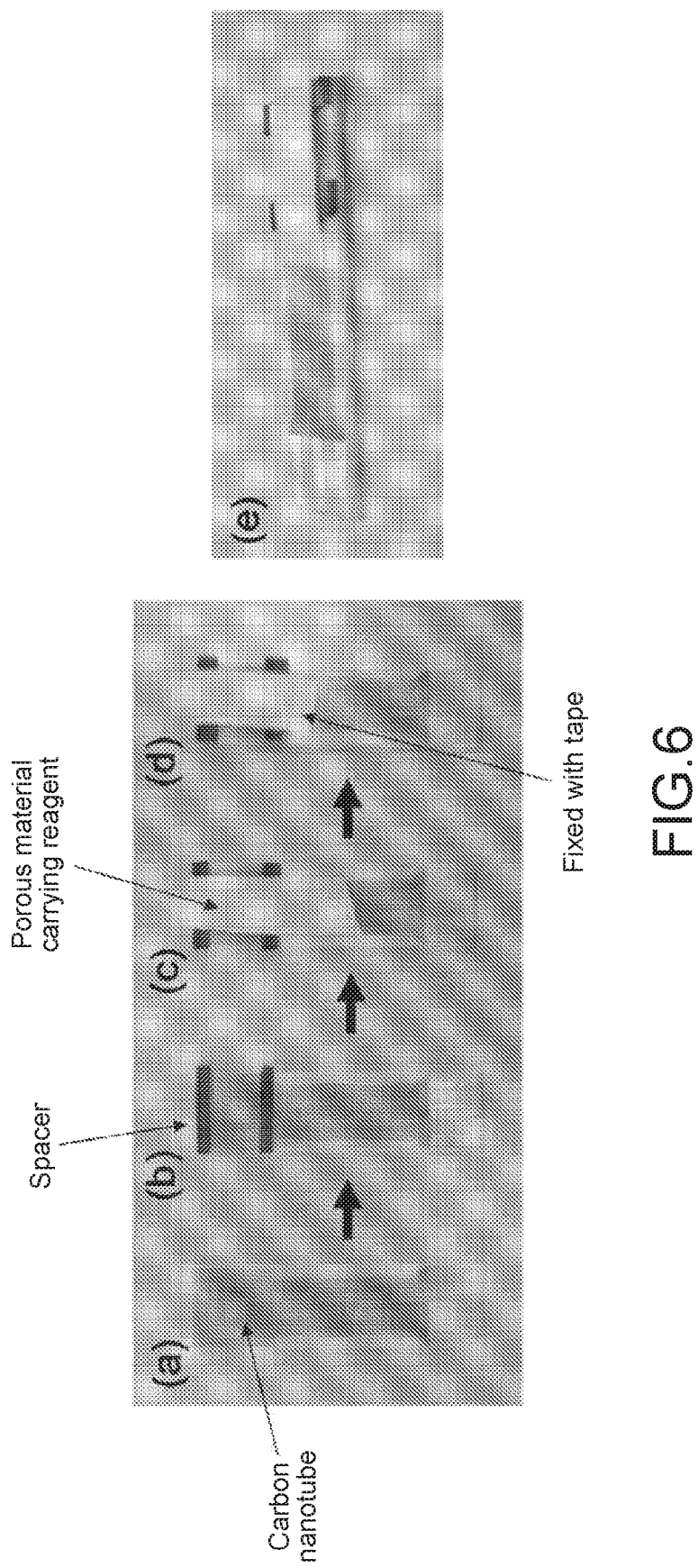
FIG. 6 is a diagram showing a state of producing the formaldehyde detecting sensor according to the present invention.

FIG. 6 is a diagram showing a state of producing the formaldehyde detecting sensor according to the present invention.

The SWCNTs (0.02 mg) was suspended in 0.2 mL of a mixed solvent of o-dichlorobenzene (o-DCB) and toluene. Note that o-DCB and toluene were mixed at a ratio of 4:1 (volume ratio). The suspension was sonicated for 30 minutes at room temperature. The suspension (approximately 0.5 μL) was drop-cast on a comb electrode, and the solvent was removed by drying. Drop-casting was repeated until the electrical resistance value of the network structure of the SWCNTs reached a predetermined value. The electrical resistance value was measured with an ohmmeter. In this way, a response unit (150 in FIG. 1) of the sensor was produced (part (a) of FIG. 6). Subsequently, a spacer (170 in FIG. 1), which had a height of 0.4 mm and was formed of a vinyl tape material, was positioned on the response unit (Part (b) of FIG. 6).

$NH_2OH \cdot HCl$ was added to methanol until being saturated (approximately 100 mg/mL). This solution was drop-cast on the PVDF membrane filter (having a pore diameter of 0.2 μm, manufactured by Merck Millipore, Omnipore Membrane Filter, JGWP). The methanol was dried in the atmosphere to produce a reaction portion (120 in FIG. 1). The amount of $NH_2OH \cdot HCl$ carried on the PVDF membrane filter was approximately 0.5 mg. Note that the amount of 0.5 mg is excess as compared with formaldehyde (HCHO) present in the atmosphere in sub-ppm order. The PVDF membrane filter carrying $NH_2OH \cdot HCl$ was cut and the response unit was covered via a spacer (Part (c) of FIG. 6). The PVDF membrane filter was fixed with tape so as not to peel of (Part (d) of FIG. 6). The state of the side surface of the sensor according to Example 1 thus obtained is shown in Part (e) of FIG. 6.

The sensor according to Example 1 was connected to a power source and an ammeter to detect formaldehyde. In detail, using a test clip fixed to a glass chamber, the comb electrode of the sensor was connected to an EmStat potentiostat with a MUX16 multiplexer manufactured by PalmSens to detect a gas. A constant potential of 0.1 V was applied to the comb electrode, and the change in the current value when the sensor was exposed to a gas was recorded using PSTrace Softwere (v.4.8).

Introduction (flowing) of air (compressed air, here) and HCHO was repeated under measurement conditions 1 to 3 shown in Table 2, and the change in the current value at that time was examined. In the present specification, a value obtained by normalizing the change in the current value by $\{(I_{(t)}-I_0)/I_0\} \times 100(\%)$ was used. Here, $I_0$ is the current value of a baseline, and $I_{(t)}$ is the current value after t seconds. The applied voltage is 0.1 V. In the present specification, this normalized value can be compared between the sensors according to Examples/Comparative Example. The results are shown in FIG. 7 to FIG. 10.

Example 2

In Example 2, the formaldehyde detecting sensor shown in FIG. 1 in which $NH_2OH \cdot HCl$ (hydroxylamine hydrochloride) and SWCNTs (including 95 weight % of a semiconductor type one and 5 weight % of a metal type one) were respectively used as the hydroxylamine salt 110 and the carbon material 130 was produced, filter paper being caused to carry the hydroxylamine salt 110 in the formaldehyde detecting sensor.

Figure 7:
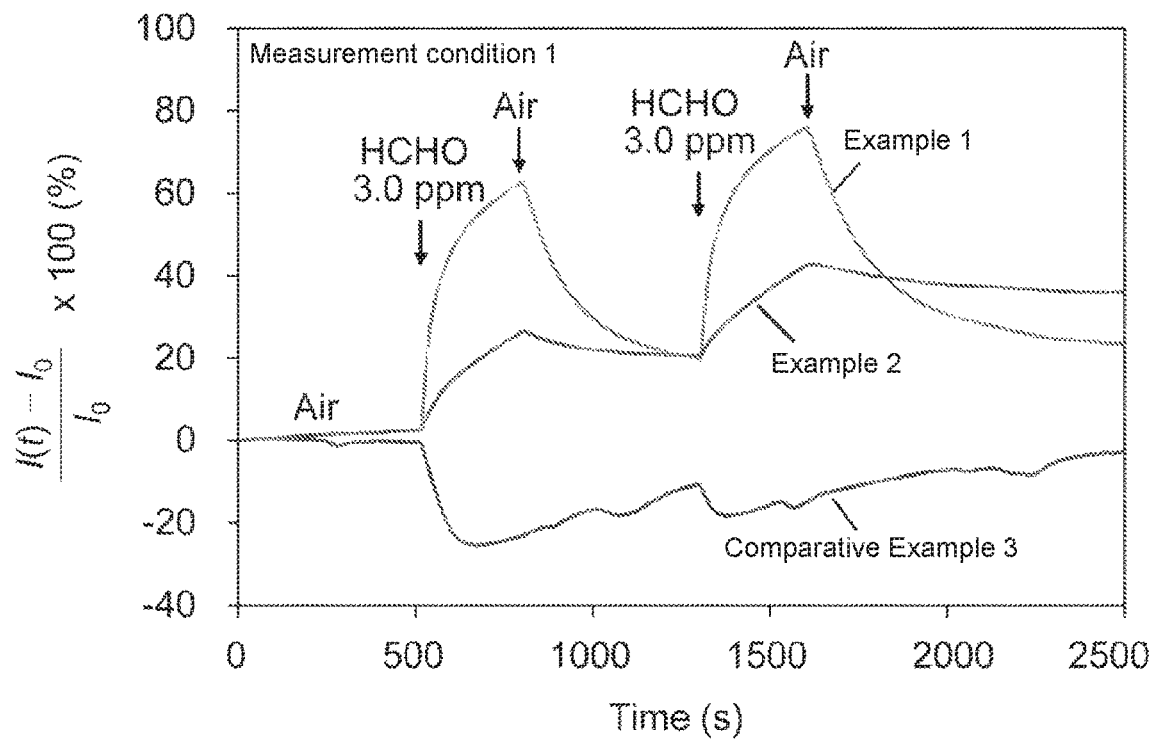
FIG. 7 is a diagram showing response characteristics of sensors according to Examples 1 and 2 and Comparative Example 3 to formaldehyde.

In Example 2, a sensor was produced in a way similar to that in Example 1 except that instead of the PVDF membrane filter in Example 1, filter paper (manufactured by Whatman, qualitative filter paper) was caused to carry $NH_2OH \cdot HCl$. Formaldehyde was detected by the sensor according to Example 2 in a procedure similar to that in Example 1 under measurement conditions 1 shown in Table 2. The results are shown in FIG. 7.

Comparative Example 3

In Comparative Example 3, $NH_2OH \cdot HCl$ (hydroxylamine hydrochloride) and SWCNTs (including 95 weight % of a semiconductor type one and 5 weight % of a metal type one) were respectively used as the hydroxylamine salt 110 and the carbon material 130, but a sensor in which the SWCNTs and $NH_2OH \cdot HCl$ are brought into contact with each other was produced.

In Comparative Example 3, a methanol solution containing $NH_2OH \cdot HCl$ was directly drop-cast on the response unit shown in Part (a) of FIG. 6, and the methanol was removed by drying. Formaldehyde was detected by the sensor according to Comparative Example 3 thus obtained in a procedure similar to that in Example 1 under the measurement conditions 1 shown in Table 2. The results are shown in FIG. 7.

Example 4

In Example 4, the formaldehyde detecting sensor shown in FIG. 1 in which o-benzhydroxylamine hydrochloride and SWCNTs (including 95 weight % of a semiconductor type one and 5 weight % of a metal type one) were respectively used as the hydroxylamine salt 110 and the carbon material 130 was produced, the PVDF membrane filter being caused to carry the hydroxylamine salt 110 in the formaldehyde detecting sensor.

Figure 8:
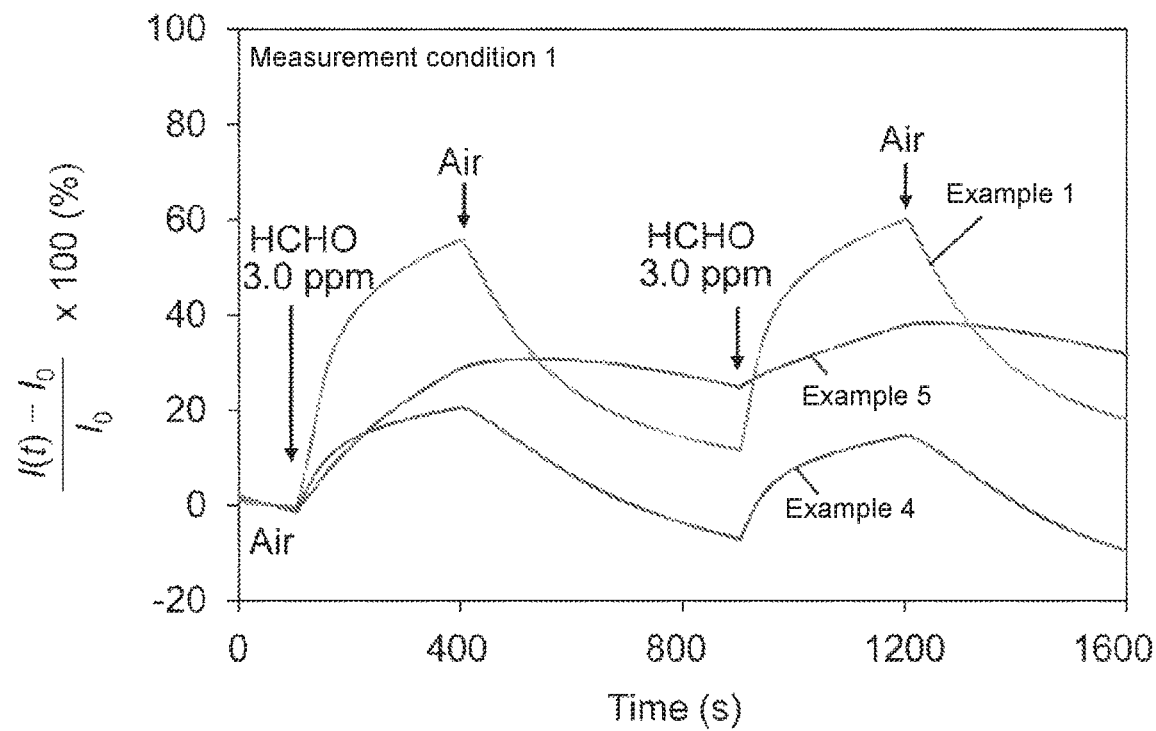
FIG. 8 is a diagram showing response characteristics of sensors according to Examples 1, 4 and 5 to formaldehyde.

In Example 4, a sensor was produced in a way similar to that in Example 1 except that o-benzhydroxylamine hydrochloride was used instead of $NH_2OH \cdot HCl$ in Example 1. The o-benzhydroxylamine hydrochloride was dissolved in methanol (67 mg/mL). The amount of the o-benzhydroxylamine hydrochloride carried on the PVDF membrane filter was approximately 0.5 mg. Formaldehyde was detected by the sensor according to Example 4 in a procedure similar to that in Example 1 under the measurement conditions 1 shown in Table 2. The results are shown in FIG. 8.

Example 5

In Example 5, the formaldehyde detecting sensor shown in FIG. 1 in which o-4 -nitrobenzenehydroxylamine hydrochloride and SWCNTs (including 95 weight % of a semiconductor type one and 5 weight % of a metal type one) were used as the hydroxylamine salt 110 and the carbon material 130 and the PVDF membrane filter was caused to carry the hydroxylamine salt 110 was produced.

In Example 5, a sensor was produced in a way similar to that in Example 1 except that o-4-nitrobenzenehydroxylamine hydrochloride was used instead of $NH_2OH \cdot HCl$ in Example 1. The o-4-nitrobenzenehydroxylamine hydrochloride was dissolved in methanol (20 mg/mL). The amount of the o-4-nitrobenzenehydroxylamine hydrochloride carried on the PVDF membrane filter was approximately 0.5 mg. Formaldehyde was detected by the sensor according to Example 5 in a procedure similar to that in Example 1 under the measurement conditions 1 shown in Table 2. The results are shown in FIG. 8.

Example 6

Figure 9:
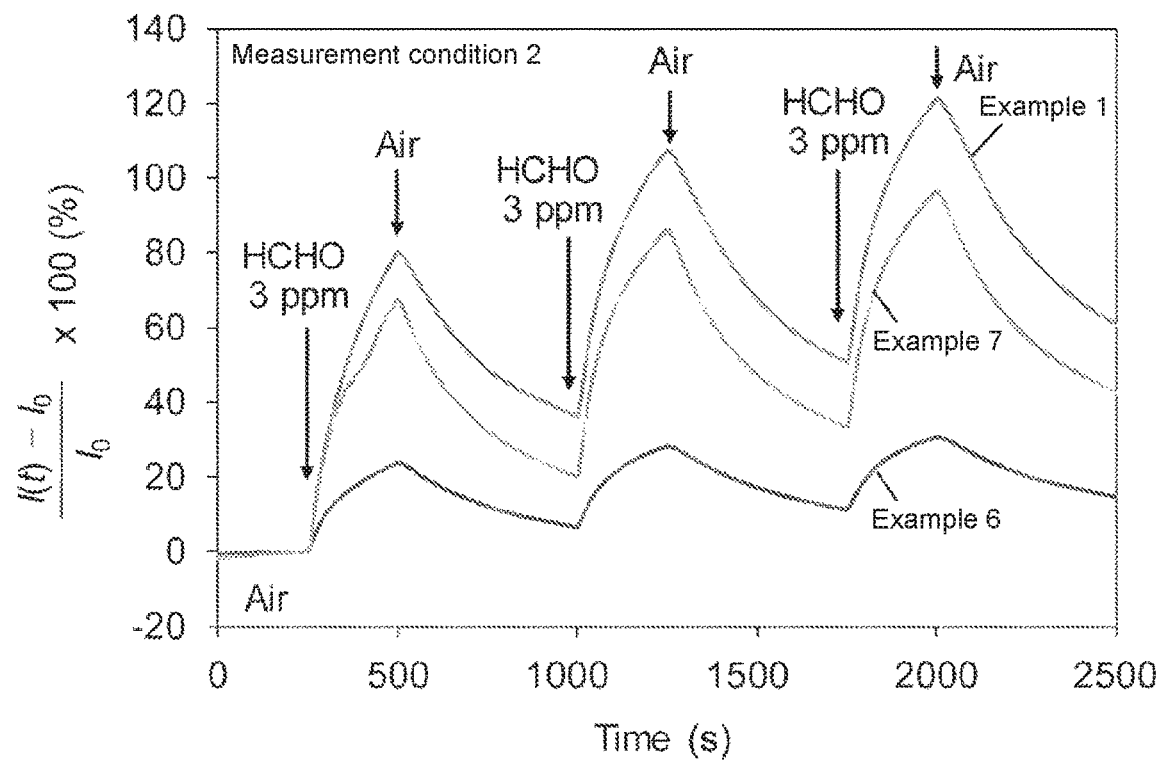
FIG. 9 is a diagram showing response characteristics of sensors according to Examples 1, 6 and 7 to formaldehyde.

In Example 6, the formaldehyde detecting sensor shown in FIG. 1 in which $NH_2OH \cdot HCl$ and SWCNTs (including 10 weight % of a semiconductor type one and 90 weight % of a metal type one) were used as the hydroxylamine salt 110 and the carbon material 130 was produced in a procedure similar to that in Example 1, the PVDF membrane filter being caused to carry the hydroxylamine salt 110 in the formaldehyde detecting sensor. Formaldehyde was detected by the sensor according to Example 6 in a procedure similar to that in Example 1 under the measurement conditions 2 shown in Table 2. The results are shown in FIG. 9.

Example 7

In Example 7, the formaldehyde detecting sensor shown in FIG. 1 in which $NH_2OH \cdot HCl$ and SWCNTs (including 66.7 weight % of a semiconductor type one and 33.3 weight % of a metal type one) were respectively used as the hydroxylamine salt 110 and the carbon material 130 was produced in a procedure similar to that in Example 1, the PVDF membrane filter being caused to carry the hydroxylamine salt 110 in the formaldehyde detecting sensor. Formaldehyde was detected by the sensor according to Example 7 in a procedure similar to that in Example 1 under the measurement conditions 2 shown in Table 2. The results are shown in FIG. 9.

Example 8

In Example 8, the formaldehyde detecting sensor shown in FIG. 1 in which $NH_2OH \cdot HCl$ (hydroxylamine hydrochloride) and SWCNTs (including 95 weight % of a semiconductor type one and 5 weight % of a metal type one) coated with a supramolecular polymer were respectively used as the hydroxylamine salt 110 and the carbon material 130 was produced, the PVDF membrane filter being caused to carry the hydroxylamine salt 110 in the formaldehyde detecting sensor.

The SWCNTs coated with a supramolecular polymer was prepared as follows. The SWCNTs (0.02 mg) and anthracene-based ligand (0.1 mg) were suspended in 0.2 mL of a mixed solvent of o-dichlorobenzene (o-DCB) and toluene. Note that the o-DCB and toluene were mixed at a ratio of 4:1 (volume ratio). Subsequently, a methanol solution (10.6 mM, 16.4 µL) in which copper acetate monohydrate was dissolved was added thereto to form the above-mentioned supramolecular polymer. The suspension was sonicated for 30 minutes at room temperature. Subsequently, the suspension was applied to a centrifuge (6238×g, 10000 rpm, 15 minutes, Rev Spin 102 manufactured by Revolutionary Science). The supernatant (top 50%) was collected to obtain a suspension containing SWCNTs coated with the supramolecular polymer. Since the subsequent procedures are similar to those in Example 1, description thereof will be omitted.

Formaldehyde was detected by the sensor according to Example 8 thus obtained in a procedure similar to that in Example 1 and measurement conditions 3 to 14 shown in Table 2. The results are shown in FIG. 10 to FIG. 24.

Reference Example 9

Figure 11:
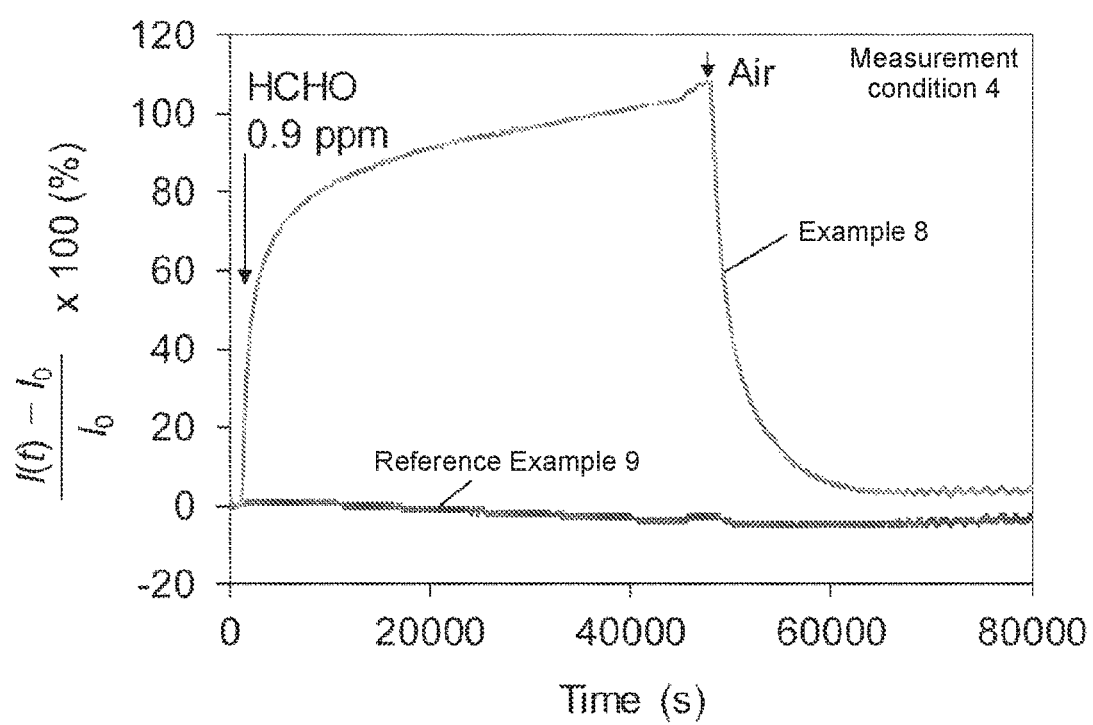
FIG. 11 is a diagram showing response characteristics of sensors according to Example 8 and Reference Example 9 to formaldehyde.
Figure 23:
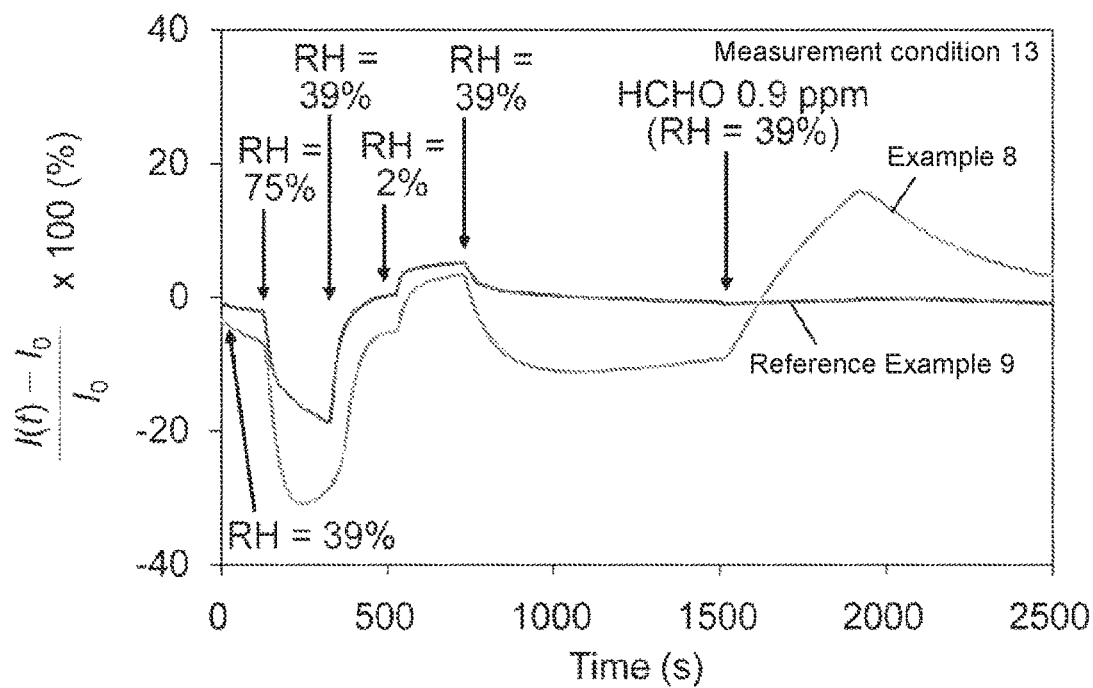
FIG. 23 is a diagram comparing the change in relative humidity and response to formaldehyde between the sensors according to Example 8 and Reference Example 9.
Figure 24:
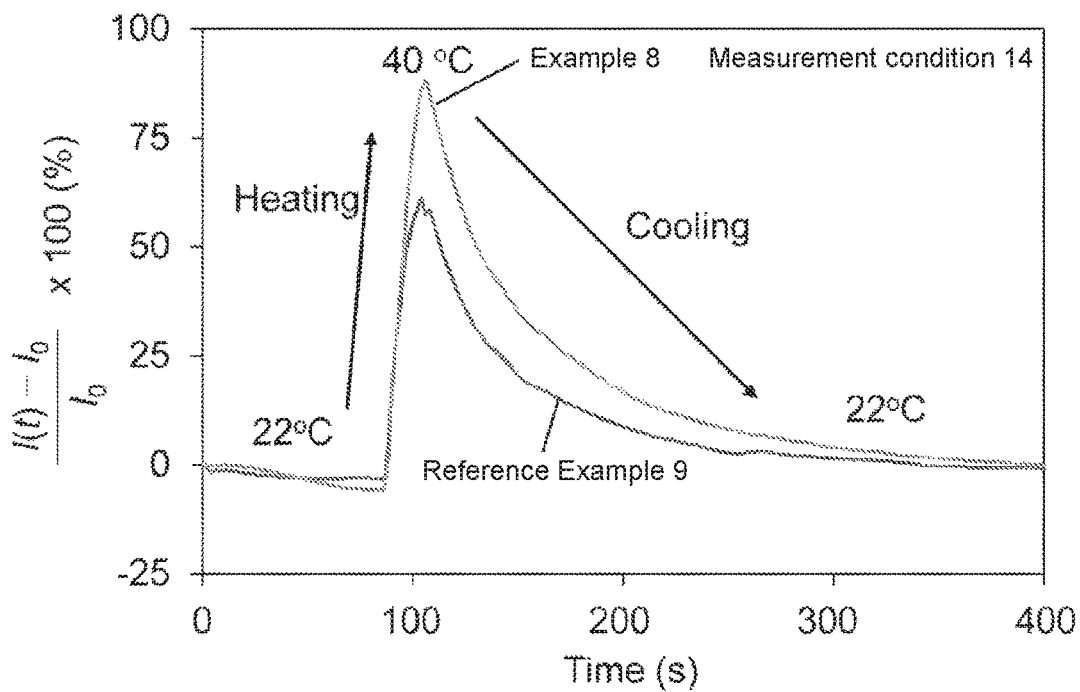
FIG. 24 is a diagram comparing the response to a temperature change between the sensors according to Example 8 and Reference Example 9.

In Reference Example 9, a formaldehyde non-detection sensor was produced in a procedure similar to that in Example 8 except that the hydroxylamine salt 110 was not used. Formaldehyde was detected by the sensor according to Reference Example 9 thus obtained in a procedure similar to that in Example 1 and the measurement conditions 4, 13, and 14 shown in Table 2. The results are shown in FIG. 11, FIG. 23, and FIG. 24.

Example 10

In Example 10, the formaldehyde detecting sensor 300 shown in FIGS. 3A-3B was produced, a polystyrene particle represented by the following formula and SWCNTs (including 95 weight % of a semiconductor type one and 5 weight % of a metal type one) coated with a supramolecular polymer being respectively used as the hydroxylamine salt 110 and the carbon material 130 in the formaldehyde detecting sensor 300, a hydroxylamine salt being modified into the polystyrene particle.

The polystyrene particle modified by a hydroxylamine salt was prepared as follows. One hundred mg of polystyrene particles modified by a hydroxylamine derivative represented by the following formula (641014-5G manufactured by Sigma-Aldrich, 100 to 200 mesh, the amount of modification 1.0 to 1.5 mmol/g, crosslinked with 1% divinylbenzene) was stirred in a 3% hydrochloric acid methanol solution (20 mL) at room temperature for one hour to convert hydroxylamine into a salt of hydrochloric acid. Subsequently, the mixture was filtered through a glass filter, and the excess hydrochloric acid was sufficiently washed with a large amount of methanol, followed by vacuum drying for one hour to obtain particles modified by a hydroxylamine salt.

(Chem. 5)

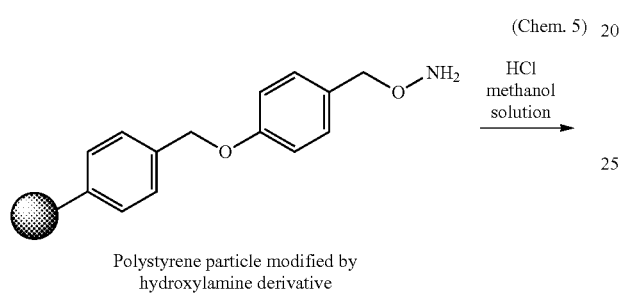

Polystyrene particle modified by hydroxylamine derivative $\xrightarrow{\text{HCl methanol solution}}$

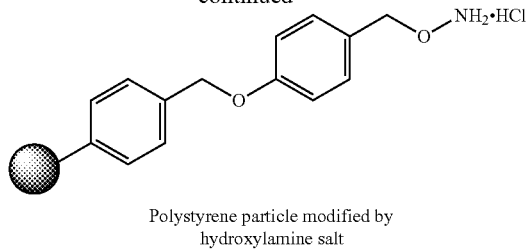

Polystyrene particle modified by hydroxylamine salt

Figure 25:
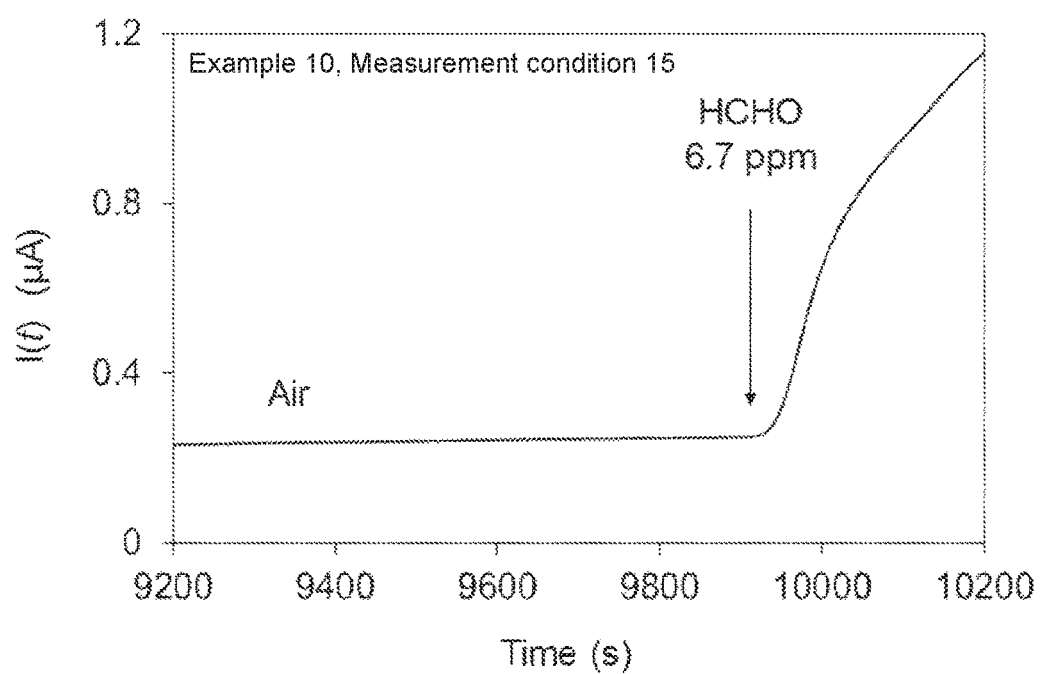
FIG. 25 is a diagram showing response characteristics of the sensor according to Example 10 to formaldehyde.

Particles (1 mg) modified by a hydroxylamine salt were positioned on a response unit obtained in a procedure similar to that in in Example 1. Formaldehyde was detected by the sensor according to Example 10 thus obtained in a procedure similar to Example 1 under the measurement condition 15 shown in Table 2. The results are shown in FIG. 25.

A list of the above-mentioned sensors according to Examples, Comparative Example, and Reference Example 1 to 10 and the measurement conditions are collectively shown in Table 1 and Table 2 for simplicity.

TABLE 1

| Example/ Comparative Example | Carbon material | Hydroxylamine salt | Carrier |
|---|---|---|---|
| Example 1 | CNT(95% semiconductor type) | $NH_2OH \cdot HCl$ | PVDF |
| Example 2 | CNT(95% semiconductor type) | $NH_2OH \cdot HCl$ | Paper |
| Comparative Example 3 | CNT(95% semiconductor type) | $NH_2OH \cdot HCl$ | — |
| Example 4 | CNT(95% semiconductor type) | o-benzhydroxylamine hydrochloride | PVDF |
| Example 5 | CNT(95% semiconductor type) | o-4-nitrobenzenehydroxylamine hydrochloride | PVDF |
| Example 6 | CNT(90% metal type) | $NH_2OH \cdot HCl$ | PVDF |
| Example 7 | CNT(Mixing of 66.7% semiconductor type and 33.3% metal type) | $NH_2OH \cdot HCl$ | PVDF |
| Example 8 | CNT covered with MSP (95% semiconductor type) | $NH_2OH \cdot HCl$ | PVDF |
| Reference Example 9 | CNT covered with MSP (95% semiconductor type) | — | — |
| Example 10 | CNT covered with MSP (95% semiconductor type) | Polystyrene (PS) modified by $NH_2OH \cdot HCl$ divinylbenzene crosslinked body | PS |

List of Sensors According to Examples, Comparative Example, and Reference Example

TABLE 2

| Measurement condition | Gas type | Concentration(ppm) | Flow rate(mL/min) | Temperature(° C.) | Relative humidity(%) |
|---|---|---|---|---|---|
| 1 | HCHO | 3 | 300 | 23 ± 1 | 38 ± 2 |
| 2 | HCHO | 3 | 300 | 22.3 | 39.2 |
| 3 | HCHO | 0.9 | 300 | 22 | 34.5 |
| 4 | HCHO | 0.9 | 300 | 22.2 ± 1 | 36.2 ± 1.3 |
| 5 | HCHO | 0.05-6.7 | 300 | 21.5 ± 0.8 | 36.7 ± 1.0 |
| 6 | HCHO | 0.9 | 300 | 22.2 | 1.5-68 |
| 7 | $H_2O$ | 420 | 300 | 22 ± 0.5 | 38.8 ± 1 |
| 8 | $H_2O$ | 3200 | 300 | 22 ± 0.5 | 38.8 ± 1 |
| 9 | MeOH | 1200 | 300 | 22 ± 0.5 | 38.8 ± 1 |
| 10 | EtOH | 440 | 300 | 22 ± 0.5 | 38.8 ± 1 |

TABLE 2-continued

List of Measurement Conditions

| Measurement condition | Gas type | Concentration(ppm) | Flow rate(mL/min) | Temperature(° C.) | Relative humidity(%) |
|---|---|---|---|---|---|
| 11 | THF | 860 | 300 | 22 ± 0.5 | 38.8 ± 1 |
| 12 | Toluene | 720 | 300 | 22 ± 0.5 | 38.8 ± 1 |
| 13 | HCHO | 0.9 | 300 | 21.6 ± 0.5 | 2-75 |
| 14 | HCHO | 0 | 300 | 22-40 | 39 |
| 15 | HCHO | 6.7 | 300 | 22 ± 0.5 | 65 ± 1 |

FIG. 7 is a diagram showing response characteristics of the sensors according to Examples 1 and 2 and Comparative Example 3 to formaldehyde.

In accordance with FIG. 7, the sensor according to Example 1 exhibited behavior in which the current value showed a positive change when formaldehyde was introduced thereinto and the current value returned to the original value when air was caused to flow thereto. The sensor according to Example 2 exhibited behavior in which the current values returned to the original value similarly to the sensor according to Example 1 although the amount of change in the current value when formaldehyde was introduced was small and the returning speed of the current value when air was caused to flow was lower as compared with the sensor according to Example 1.

Meanwhile, the sensor according to Comparative Example 3 did not show a reversible response when air and formaldehyde were caused to flow thereto.

These showed that the formaldehyde detecting sensor according to the present invention was capable of detecting formaldehyde reversibly with favorable reproducibility because it includes: a reaction portion that contains at least a hydroxylamine salt and reacts with formaldehyde to generate an acid; and a response unit that includes an electrode carrying a carbon material, an electrical resistance value of the carbon material varying, in which the hydroxylamine salt and the carbon material are separated from each other.

FIG. 8 is a diagram showing response characteristics of the sensors according to Examples 1, 4 and 5 to formaldehyde.

In accordance with FIG. 8, all of the sensors according to Examples 1, 4, and 5 exhibited behavior in which the current value showed a positive change when formaldehyde was introduced thereinto and the current value returned to the original value when air was caused to flow thereto. Among them, the sensor according to Example 1 showed the largest change in the current value.

From these, it was confirmed that the hydroxylamine salt of the reaction portion is capable of detecting formaldehyde regardless of the type of the hydroxylamine salt. It was found that among the hydroxylamine salts, hydroxylamine hydrochloride was excellent in sensitivity to formaldehyde and repetition characteristics.

FIG. 9 is a diagram showing response characteristics of the sensors according to Examples 1, 6 and 7 to formaldehyde.

In accordance with 9, all of the sensors according to Examples 1, 6, and 7 exhibited behavior in which the current value showed a positive change when formaldehyde was introduced thereinto and the current value returned to the original value when air was caused to flow thereto. Among them, the sensor according to Example 1 showed the largest change in the current value.

These showed that from the viewpoint of improving the sensitivity to formaldehyde, the carbon material of the response unit favorably contained at least a semiconductor type one among the carbon nanotubes and the amount of the semiconductor type one is favorably 60 weight % or more.

Figure 10:
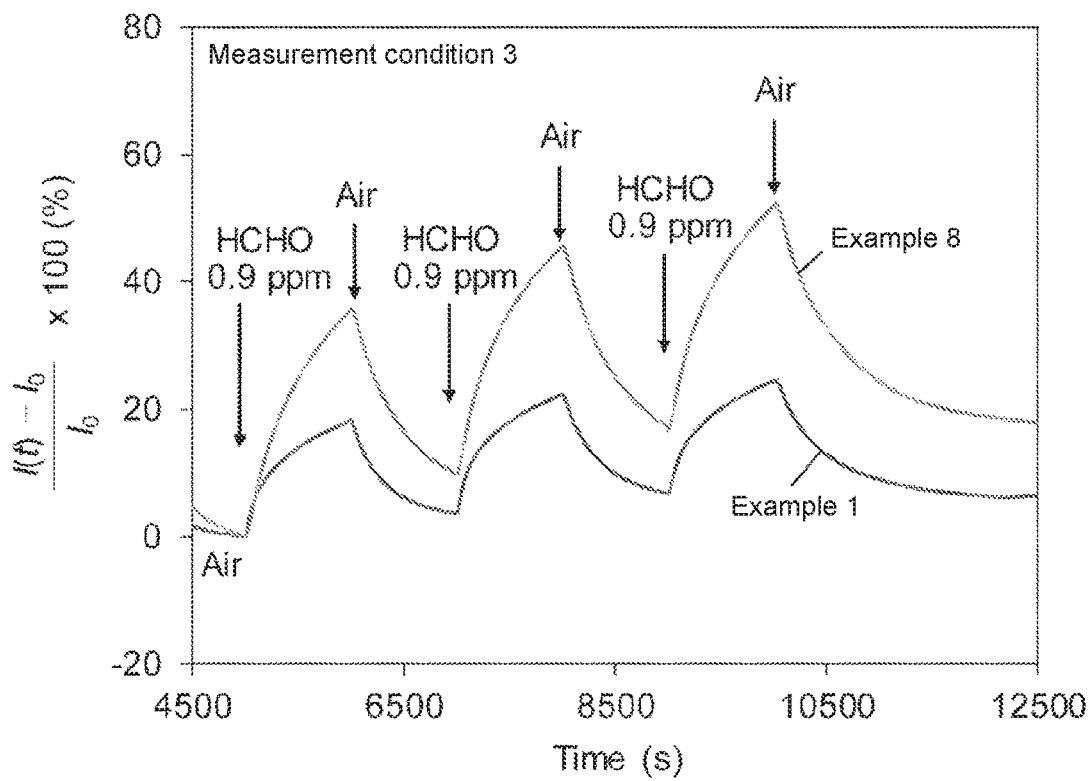
FIG. 10 is a diagram showing response characteristics of sensors according to Examples 1 and 8 to formaldehyde.

FIG. 10 is a diagram showing response characteristics of the sensors according to Examples 1 and 8 to formaldehyde.

In accordance with FIG. 10, all of the sensors according to Examples 1 and 8 exhibited behavior in which the current value showed a positive change when formaldehyde was introduced thereinto and the current value returned to the original value when air was caused to flow thereto. Among them, the sensor according to Example 8 showed the largest change in the current value. This is presumably because by coating the carbon nanotube with the supramolecular polymer, the carbon nanotube had a more dispersed network structure, the specific surface area increased, and the reaction with an acid proceeded.

These showed that from the viewpoint of improving the sensitivity to formaldehyde, the carbon material of the response unit was favorably coated with a dispersion medium such as a supramolecular polymer.

FIG. 11 is a diagram showing response characteristics of the sensors according to Example 8 and Reference Example 9 to formaldehyde.

In accordance with FIG. 11, the sensor according to Reference Example 9 did not respond to formaldehyde at all and functioned as a formaldehyde non-detection sensor. Meanwhile, the sensor according to Example 8 responded to formaldehyde, and the current value positively increased but returned to the original value when air was caused to flow thereto. Also these showed that the sensor according to the present invention was effective for repeated detection of formaldehyde and capable of constantly monitoring formaldehyde.

Figure 12:
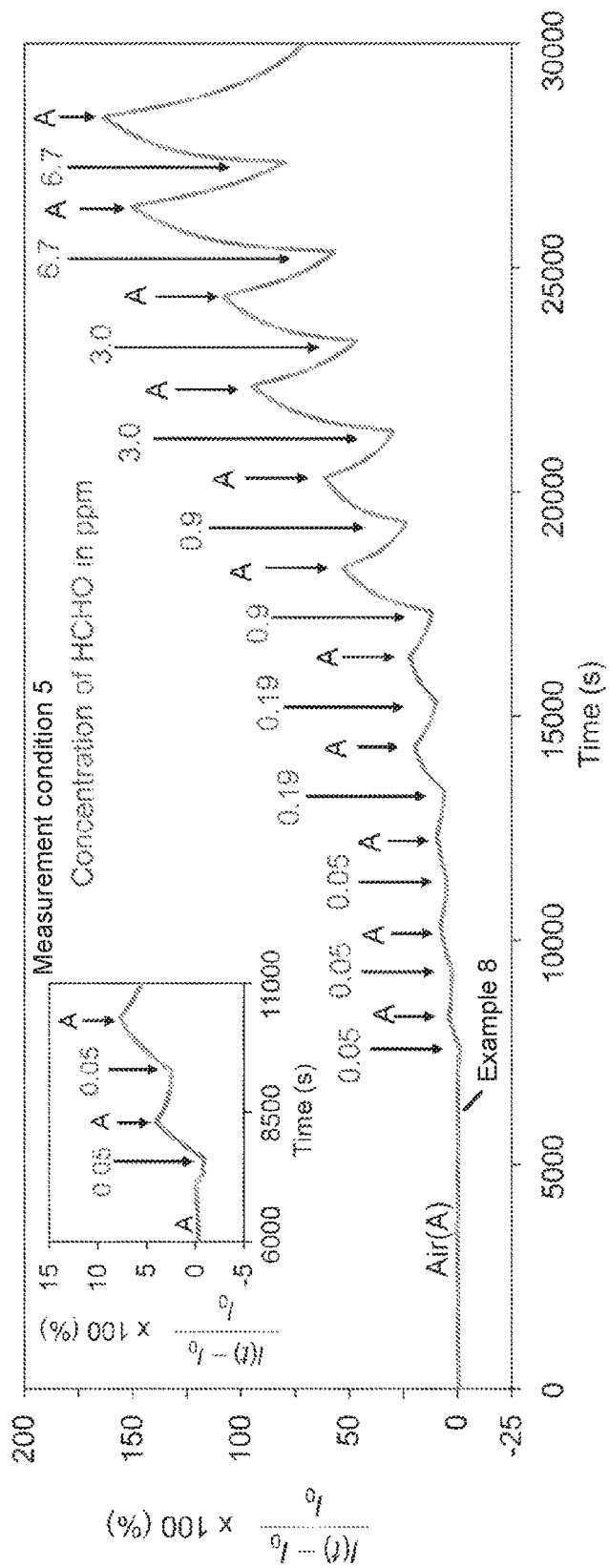
FIG. 12 is a diagram showing the formaldehyde concentration dependence of the response characteristics of the sensor according to Example 8 to formaldehyde.

FIG. 12 is a diagram showing the formaldehyde concentration dependence of the response characteristics of the sensor according to Example 8 to formaldehyde.

Figure 13:
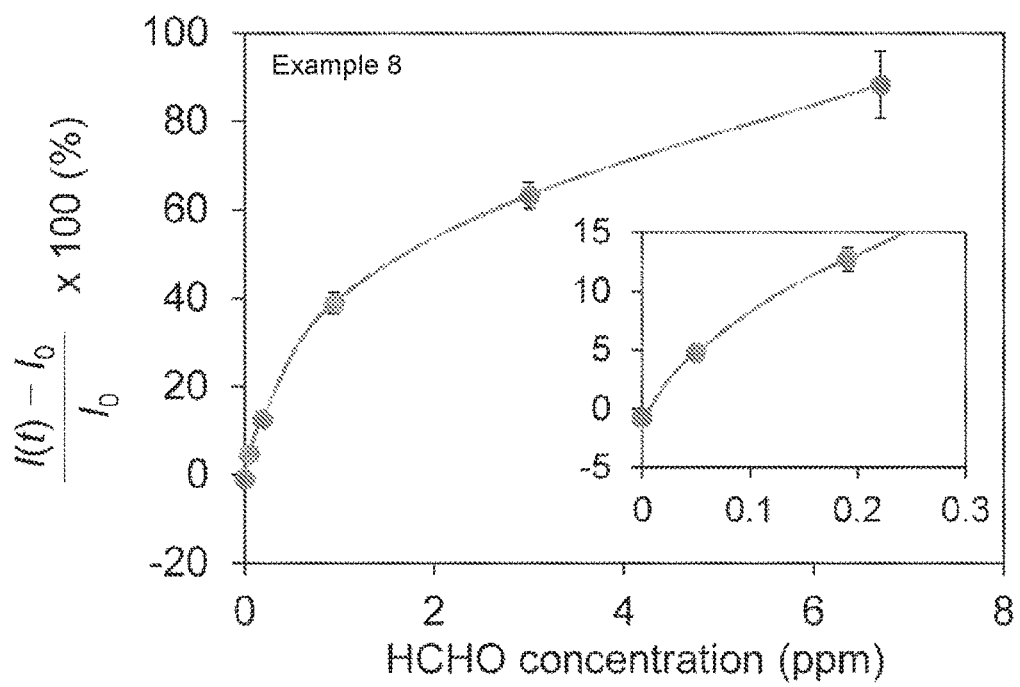
FIG. 13 is a diagram showing the correlation between the formaldehyde concentration and the increase in current value in the sensor according to Example 8 based on FIG. 12.

FIG. 13 is a diagram showing the correlation between the formaldehyde concentration and the increase in current value in the sensor according to Example 8 based on FIG. 12.

Figure 14:
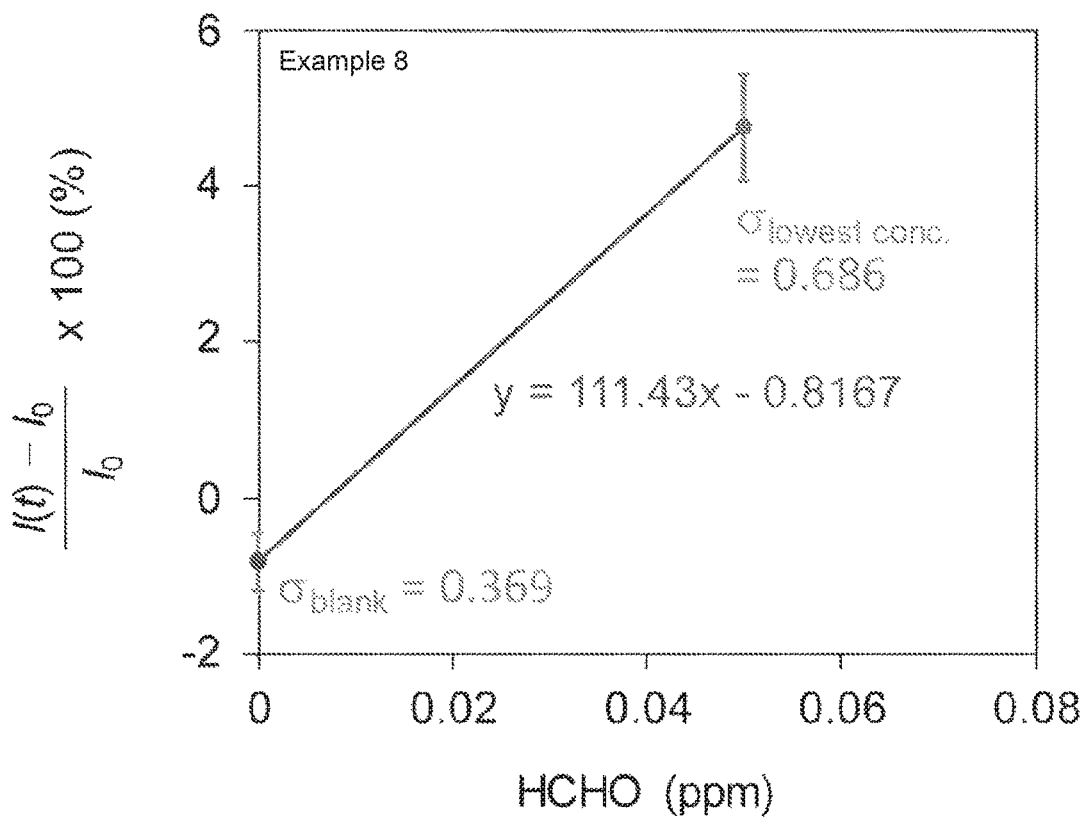
FIG. 14 is an enlarged view of a part of FIG. 13.

FIG. 14 is an enlarged view of a part of FIG. 13. FIG. 14 shows the standard deviation of the change in the current value when the formaldehyde concentration is 0 ppm and 0.05 ppm.

In accordance with FIG. 12, the sensor according to Example 8 responded to formaldehyde even at an extremely low concentration of 0.05 ppm and showed a change in the current value. This showed that the sensor according to the present invention was capable of detecting formaldehyde at a concentration below the standard (0.08 ppm) for formaldehyde of WHO. Note that the above-mentioned concentration of 0.05 ppm corresponded to the limit value of the formaldehyde concentration at which formaldehyde could be generated at a reliable concentration in this experimental system. Note that in the case where the formaldehyde concentration was 7 ppm or more, the change in the current value tended to be saturated.

From the average value (concentration of 0 ppm) of the change in the current value and the standard deviation (concentration of 0 ppm and 0.05 ppm) of the change in the current value shown in FIG. 14, the limit of detection (LoD) of the sensor according to the present invention was obtained on the basis of the following formula.

$$LoD = mean_{blank} + 1.645 \times \sigma_{blank} + 1.645 \sigma_{lowest\ conc}.$$

Here, the $mean_{blank}$ is an average value of the change in the current value of a response when air containing no formaldehyde is introduced, $\sigma_{blank}$ is a standard deviation of the change in the current value of a response when air containing no formaldehyde is introduced, and $\sigma_{lowest\ conc}$. is a standard deviation of the change in the current value of a response when formaldehyde at the lowest concentration (here, 0.05 ppm) was introduced.

The limit of detection (LoD) of the amount of change in the current value of the sensor was calculated to be 0.92%, and it was found that this value corresponded to 0.016 ppm. This showed that a trace amount of formaldehyde sufficiently lower than 0.08 ppm that was the standard of WHO could be theoretically detected by using the sensor according to the present invention and the sensor according to the present invention was extremely excellent in sensitivity to formaldehyde.

Figure 15:
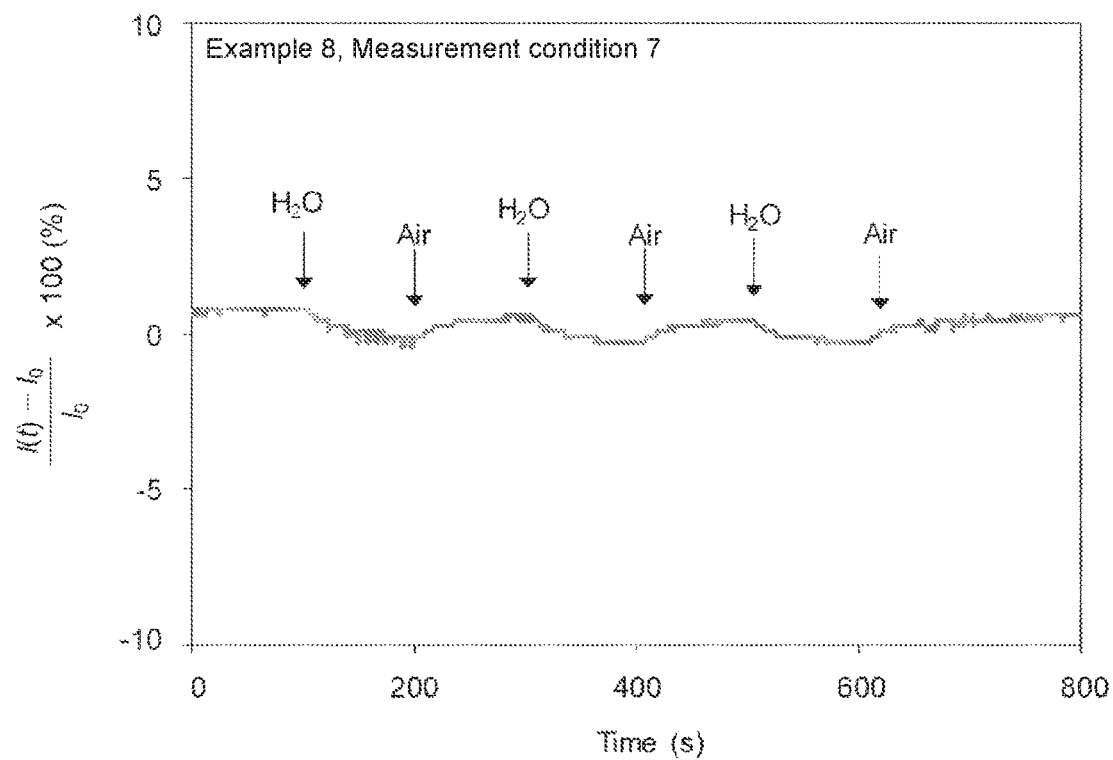
FIG. 15 is a diagram showing response characteristics of the sensor according to Example 8 to water (420 ppm).

FIG. 15 is a diagram showing response characteristics of the sensor according to Example 8 to water (420 ppm).

Figure 16:
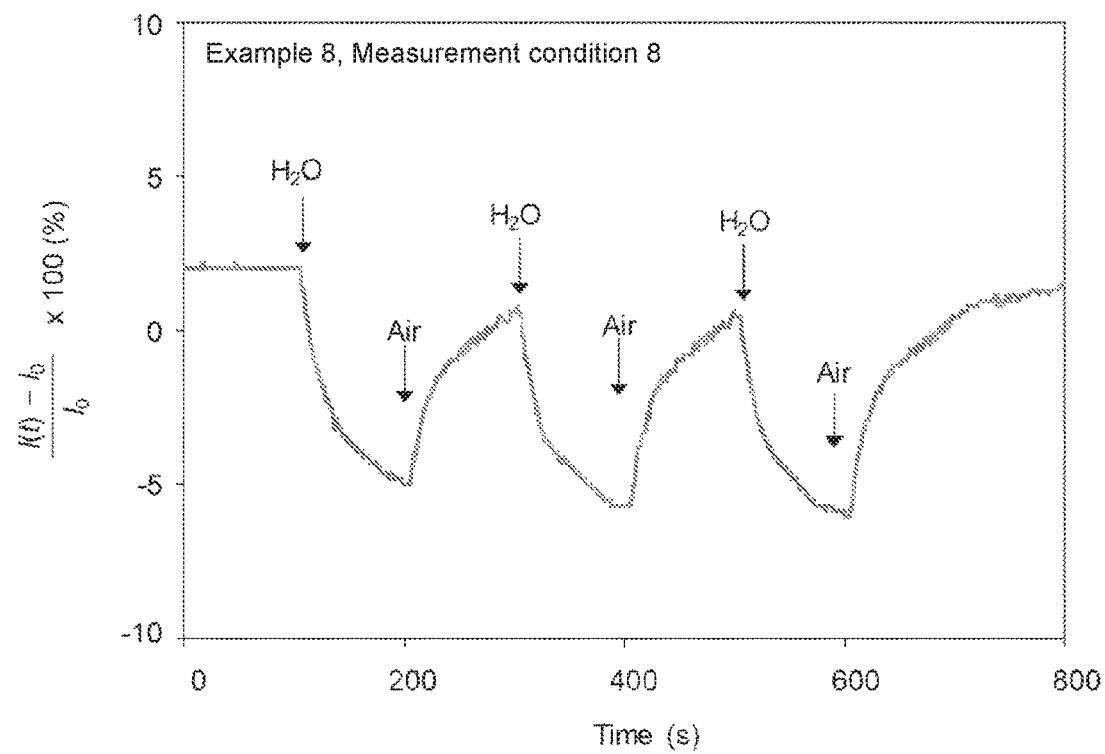
FIG. 16 is a diagram showing response characteristics of the sensor according to Example 8 to water (3200 ppm).

FIG. 16 is a diagram showing response characteristics of the sensor according to Example 8 to water (3200 ppm).

Figure 17:
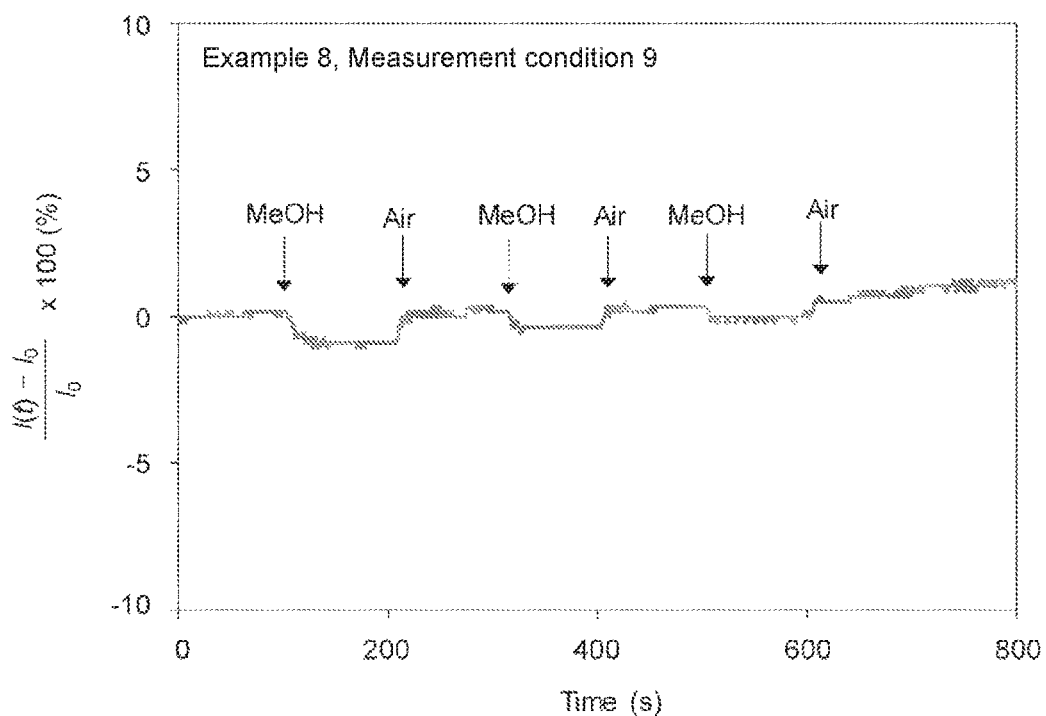
FIG. 17 is a diagram showing response characteristics of the sensor according to Example 8 to methanol (1200 ppm).

FIG. 17 is a diagram showing response characteristics of the sensor according to Example 8 to methanol (1200 ppm).

Figure 18:
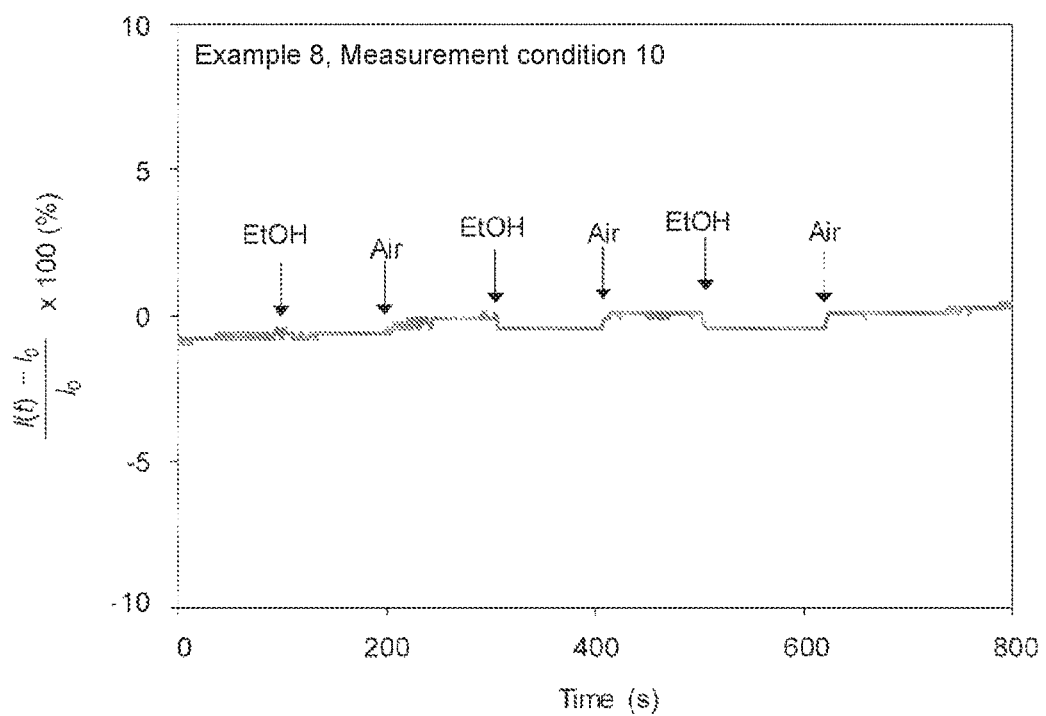
FIG. 18 is a diagram showing response characteristics of the sensor according to Example 8 to ethanol (440 ppm).

FIG. 18 is a diagram showing response characteristics of the sensor according to Example 8 to ethanol (440 ppm).

Figure 19:
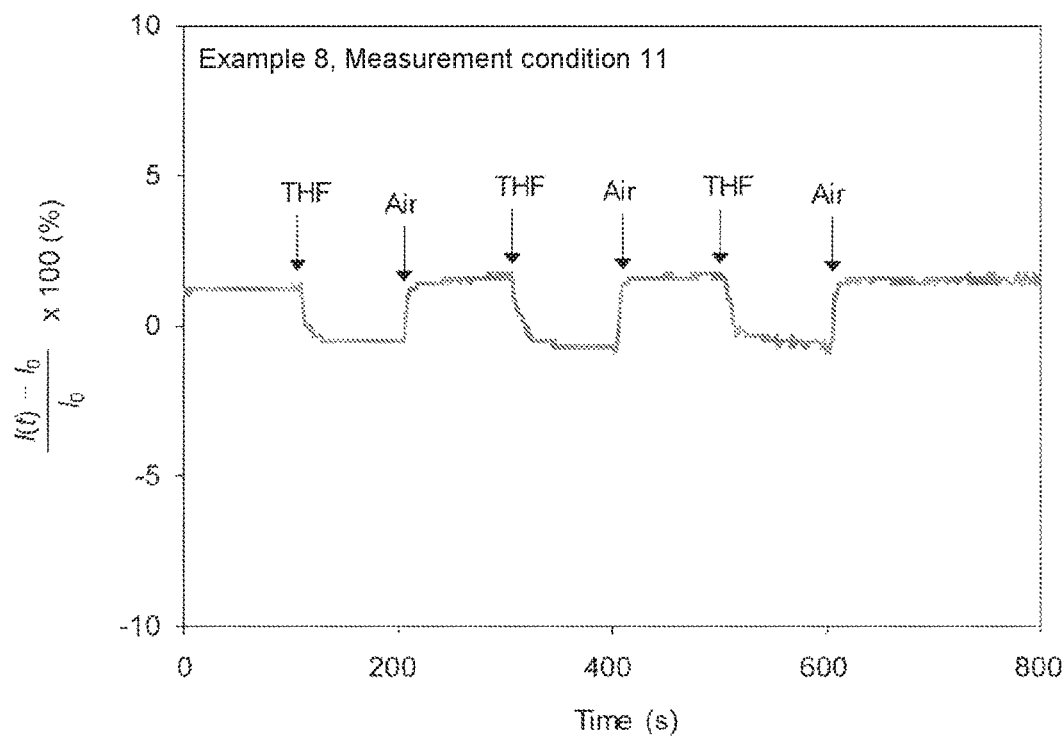
FIG. 19 is a diagram showing response characteristics of the sensor according to Example 8 to tetrahydrofuran (860 ppm).

FIG. 19 is a diagram showing response characteristics of the sensor according to Example 8 to tetrahydrofuran (860 ppm).

Figure 20:
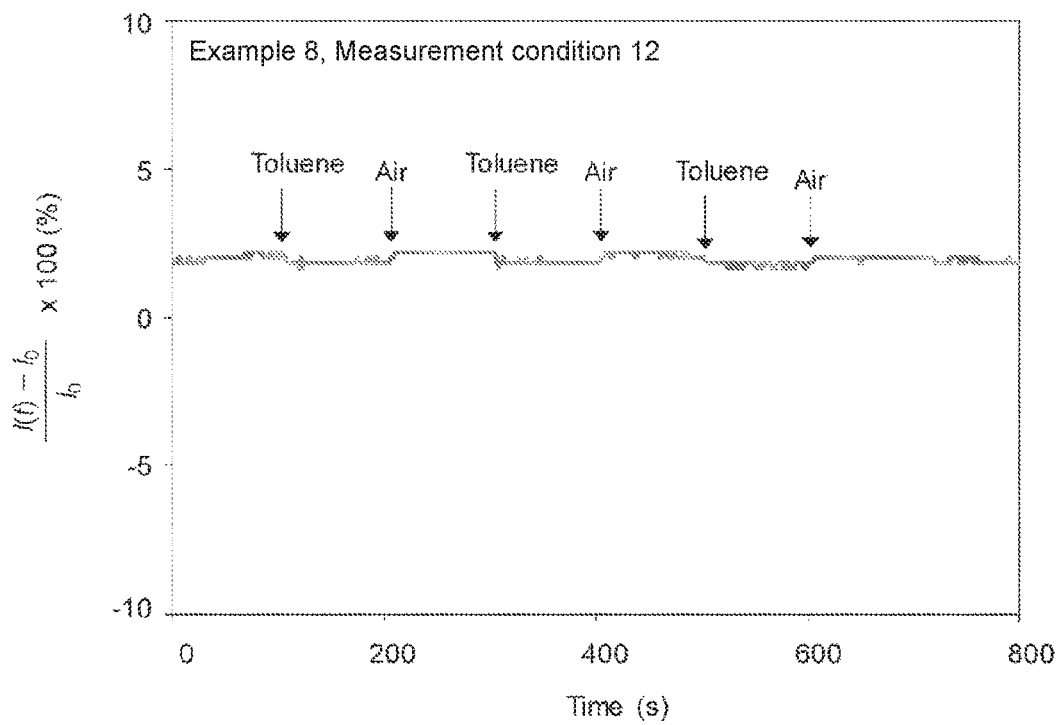
FIG. 20 is a diagram showing response characteristics of the sensor according to Example 8 to toluene (720 ppm).

FIG. 20 is a diagram showing response characteristics of the sensor according to Example 8 to toluene (720 ppm).

Figure 21:
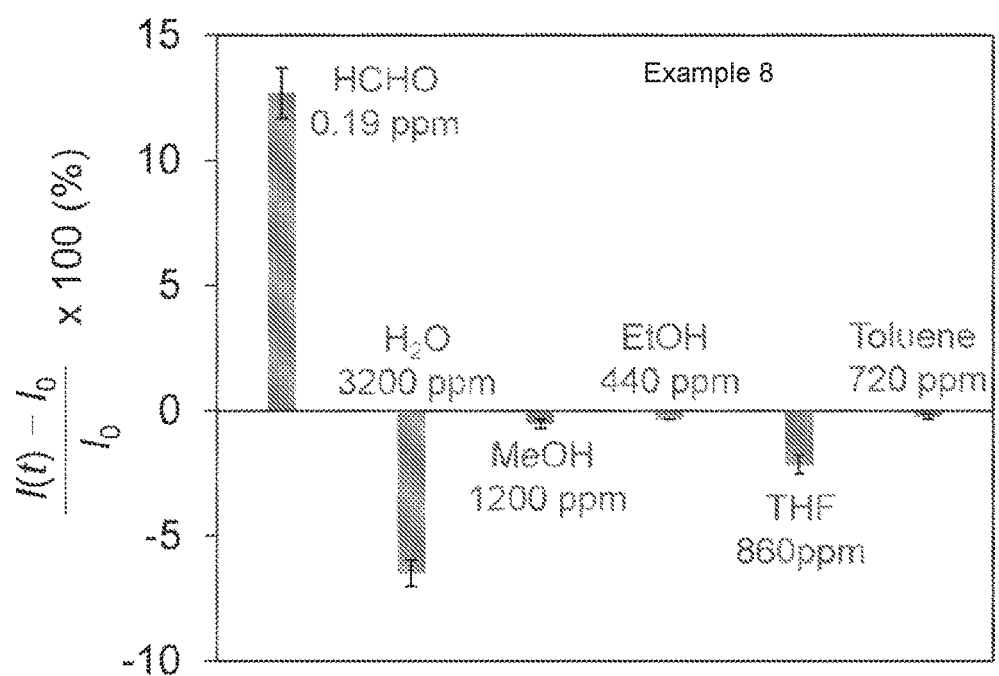
FIG. 21 is a diagram showing a list of response characteristics of the sensor according to Example 8 to various gases.

FIG. 21 is a diagram showing a list of response characteristics of the sensor according to Example 8 to various gases.

In accordance with FIG. 15 to FIG. 20, the sensor according to the present invention shows some response to various gases. Referring to FIG. 21, it can be seen that the sensor according to the present invention responses to formaldehyde selectively with high sensitivity even in the case of formaldehyde at an extremely low concentration. In detail, the sensitivity to formaldehyde at the concentration of 0.19 ppm is equal to or significantly larger than the sensitivity to other gases at the concentration of tens to hundreds of thousands of times of 0.19 ppm. This shows that the sensitivity to formaldehyde is approximately $10^4$ to $10^6$ times the sensitivity to other gases.

It should further noted that gases other than formaldehyde inject electrons into the carbon material (here, the network structure of the SWCNT) and causes it to swell, so that the sensor according to the present invention exhibited, in the case of detecting the above-mentioned gas other than formaldehyde, response characteristics (i.e., reduction in conductivity) opposite to those of formaldehyde. Also this indicates that the sensor according to the present invention is capable of detecting only formaldehyde selectively and with high accuracy.

Figure 22:
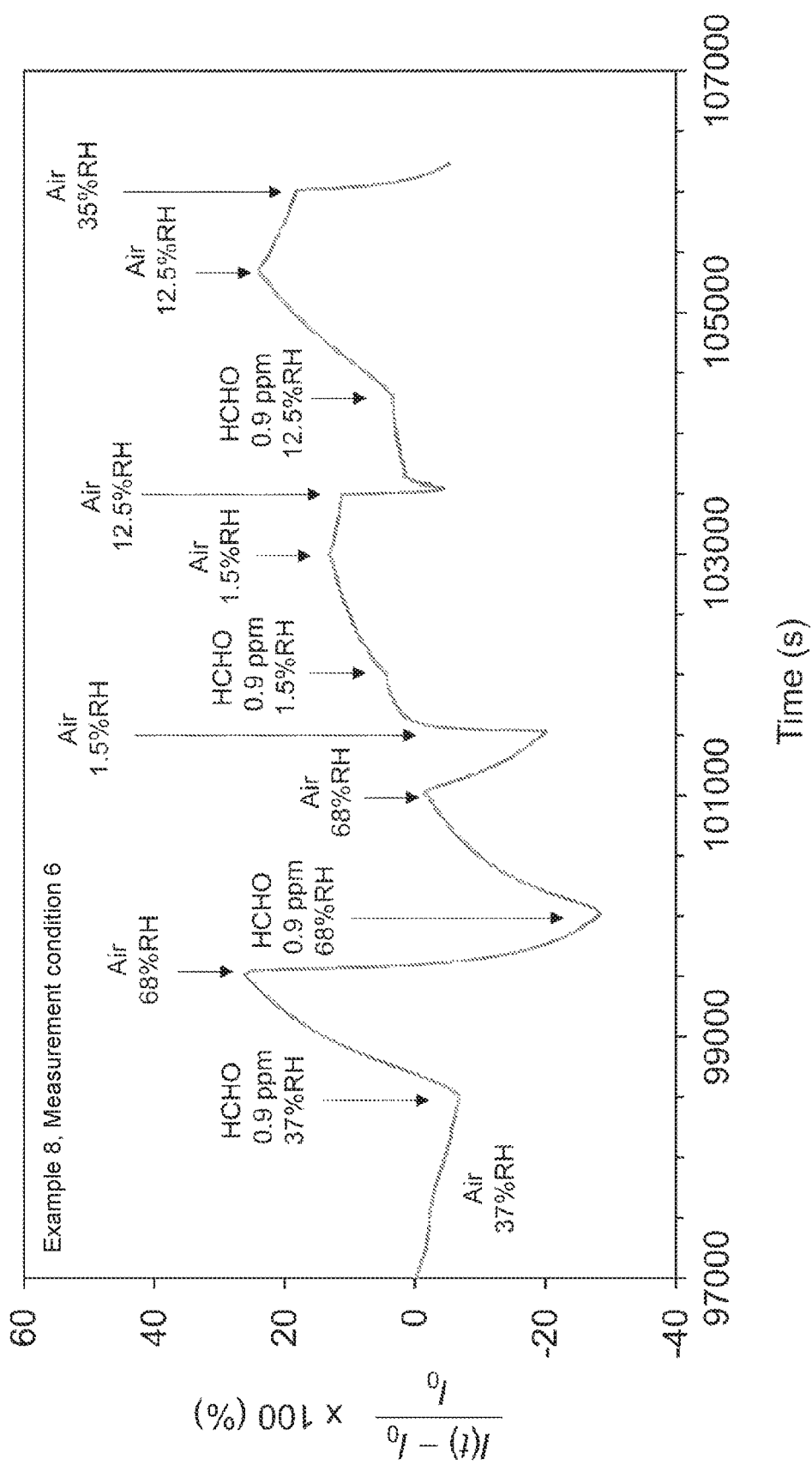
FIG. 22 is a diagram showing the influence of humidity on the response characteristics of the sensor according to Example 8.

FIG. 22 is a diagram showing the influence of humidity on the response characteristics of the sensor according to Example 8.

In accordance with FIG. 22, the sensor according to Example 8 responded to formaldehyde irrespective of the relative humidity to show a change in the current value but the sensitivity to formaldehyde was reduced as the relative humidity was lower (i.e., air was drier). However, in a normal use environment (the relative humidity is 12.5% to 68%), the influence of the humidity on the sensor according to the present invention is small and it can be said that there is no problem. Further, the relative humidity can be easily measured by a separately prepared hygrometer, and the data may be used for performing correction in the formaldehyde sensor.

FIG. 23 is a diagram comparing the change in relative humidity and response to formaldehyde between the sensors according to Example 8 and Reference Example 9.

FIG. 24 is a diagram comparing the response to a temperature change between the sensors according to Example 8 and Reference Example 9.

As described above, the response characteristics of the sensor according to the present invention depend on the relative humidity. However, in accordance with FIG. 23 and FIG. 24, it was found that the sensor according to Example 8, which includes a reaction portion that contains a hydroxylamine salt, and the sensor according to Reference Example 9, which does not includes a reaction portion, exhibited similar response tendency although the response strength differed with respect to the relative humidity and temperature. This showed that simultaneously using the formaldehyde detecting sensor and the formaldehyde non-detection sensor according to the present invention to compare the response characteristics thereof with each other makes it possible to provide a formaldehyde detecting system that easily distinguishes the correct response (response by formaldehyde) and the erroneous response (response by the relative humidity or temperature) from each other accurately. That is, it is possible to determine that formaldehyde is detected when the sensor according to Example 8 responses and the sensor according to Reference Example 9 does not respond.

FIG. 25 is a diagram showing response characteristics of the sensor according to Example 10 to formaldehyde.

In the sensor according to Example 10, the current value showed a positive change when formaldehyde was introduced thereinto. This shows that in the formaldehyde detecting sensor according to the present invention, the hydroxylamine salt of the reaction portion may be directly fixed to/carried on a solid such as a particle.

Example 11

In Example 11, the formaldehyde detecting system 500 shown in FIG. 5, which respectively includes the sensor according to Example 8, the sensor according to Reference Example 9, and a light-emitting device (LED) connected to each of the sensors according to Example 8 and Reference Example 9 as the formaldehyde detecting sensor 100, the formaldehyde non-detection sensor 510, and the detection means 410, was produced. The system according to the present invention was connected to a button battery of 3.0 V. Formaldehyde was introduced into the system according to the present invention, and a change in the LED at that time was examined. The results are shown in FIG. 26.

Figure 26:
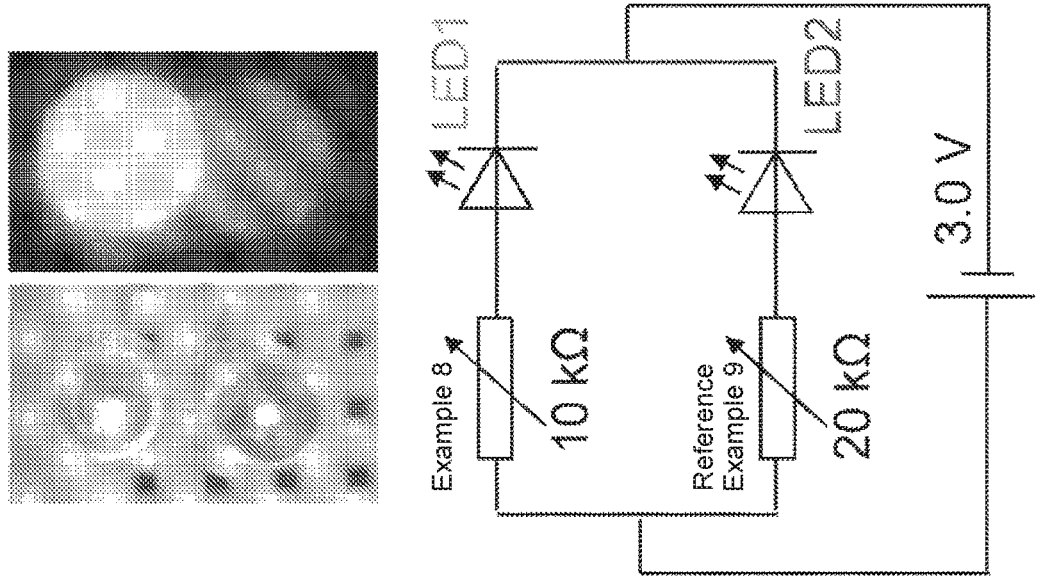
FIG. 26 is a diagram showing a formaldehyde detecting system according to Example 11 and a state of response to formaldehyde.
Figure 26:
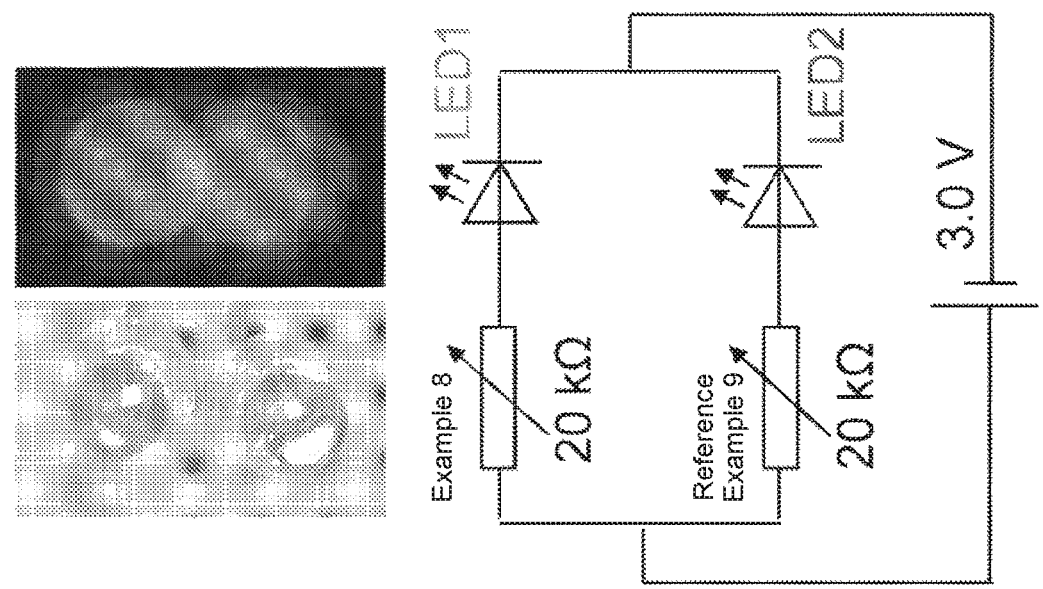

FIG. 26 is a diagram showing the formaldehyde detecting system according to Example 11 and a state of response to formaldehyde.

The resistance of each of the sensors according to Example 8 and Reference Example 9 was set to 20 kΩ. At this time, LEDs 1 and 2 were visually similar in brightness (upper left in FIG. 26). Here, when formaldehyde at the concentration of 0.9 ppm was introduced into the system, the resistance of the sensor according to Example 8 was reduced to 10 kΩ but the resistance of the sensor according to Reference Example 9 did not change. As a result, the LED 1 connected to the sensor according to Example 8 became brighter than the LED 2 connected to the sensor according to Reference Example 9 (upper right in FIG. 26). Further, as described with reference to FIG. 23 and FIG. 24, by using the sensors according to Example 8 and Reference Example 9, it is possible to distinguish the correct response and the erroneous response from each other. This showed that the system according to the present invention was capable of detecting formaldehyde selectively and with high accuracy by using the formaldehyde detecting sensor.

Example 12

Since a system according to Example 12 is similar to the system according to Example 11 except that a resistor of 20 kΩ was simply used as the formaldehyde non-detection sensor 510, description thereof is omitted. Similarly to Example 11, formaldehyde was introduced into the system and a change in the LED at that time was examined. The results are shown in FIGS. 27A-27B.

Figure 27A:
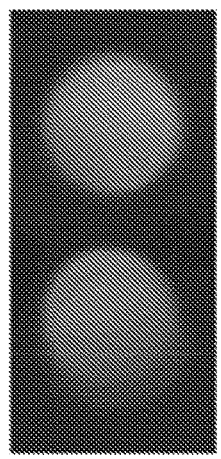
FIGS. 27A-27B are diagrams showing (FIG. 27A) a state of luminance of an LED before introducing formaldehyde and (FIG. 27B) a state of luminance of the LED after introducing formaldehyde in a system according to Example 12.
Figure 27B:
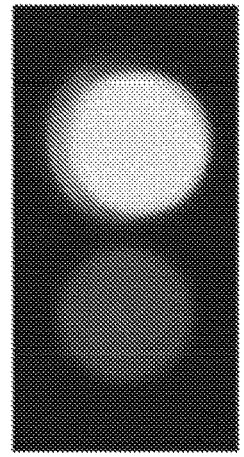

FIGS. 27A-27B are diagrams showing (FIG. 27A) a state of luminance of an LED before introducing formaldehyde and (FIG. 27B) a state of luminance of the LED after introducing formaldehyde in the system according to Example 12.

In accordance with FIGS. 27A-27B, similarly to FIG. 26, the LED 1 connected to the sensor according to Example 8 became bright and the LED 2 connected to the sensor according to Reference Example 9 did not change when formaldehyde was introduced. Also this showed that the system according to the present invention was capable of detecting formaldehyde selectively and with high accuracy by using the formaldehyde detecting sensor.

INDUSTRIAL APPLICABILITY

The formaldehyde detecting sensor according to the present invention is capable of detecting formaldehyde selectively with high accuracy under an indoor environment. The formaldehyde detecting sensor according to the present invention can function as an alarm-type detection sensor because it is capable of constantly monitoring formaldehyde. The formaldehyde detecting sensor that performs detection with such an electric resistor can be easily combined with various electronic apparatuses and detection devices, and it is possible to provide an inexpensive, small, and low power consumption formaldehyde detecting system. For example, by mounting it on a wireless communication device such as an RFID tag described in Patent Literature 3, it can be assumed that the formaldehyde sensor can be made into an IoT device or formaldehyde can be detected by general-purpose electronic apparatuses such as smartphones.

REFERENCE SIGNS LIST

100, 200, 300 formaldehyde detecting sensor
110 hydroxylamine salt
120 reaction portion
130 carbon material
140 electrode
150 response unit
160 substrate
170 spacer
310 particle
400, 500 formaldehyde detecting system
410 detection means
420 power source
510 formaldehyde non-detection sensor

The invention claimed is:

1. A formaldehyde detecting sensor, comprising:
   a reaction portion that contains at least a hydroxylamine salt and reacts with formaldehyde to generate an acid, the acid being in a gaseous state; and
   a response unit that includes an electrode carrying a carbon material, an electrical resistance value of the carbon material varying depending on the acid generated in the reaction portion,
   wherein the hydroxylamine salt and the carbon material are physically spaced apart from each other.

2. The formaldehyde detecting sensor according to claim 1, wherein the hydroxylamine salt is a neutralized salt selected from the group consisting of a halogenate, a nitrate, a sulfate, a phosphate, a borate, and a trifluoroacetate of hydroxylamine ($NH_2OH$).

3. The formaldehyde detecting sensor according to claim 1, wherein the hydroxylamine salt is a neutralized salt selected from the group consisting of a halogenate, a nitrate, a sulfate, a phosphate, a borate, and a trifluoroacetate of $NH_2OR$ (R is an aromatic, cyclic, or acyclic hydrocarbon compound or a derivative thereof).

4. The formaldehyde detecting sensor according to claim 1, wherein the carbon material is selected from the group consisting of a carbon nanotube, a carbon nanohorn, graphene, and fullerene.

5. The formaldehyde detecting sensor according to claim 4, wherein the carbon nanotube contains 10 weight % or more of a semiconductor carbon nanotube.

6. The formaldehyde detecting sensor according to claim 5, wherein the carbon nanotube contains 60 weight % or more of the semiconductor type-carbon nanotube.

7. The formaldehyde detecting sensor according to claim 1, wherein the carbon material is coated with a dispersant selected from the group consisting of a π-conjugated low molecule, a surfactant, a polymer, and a supramolecular polymer; wherein the π-conjugated low molecule is pyrene, anthracene, or porphyrin.

8. The formaldehyde detecting sensor according to claim 1, wherein the hydroxylamine salt is carried on a porous material.

9. The formaldehyde detecting sensor according to claim 8, wherein the porous material is selected from the group consisting of paper, a hydrophobic polymer, a hydrophilic polymer, porous glass, a porous carbon material, and porous oxide.

10. The formaldehyde detecting sensor according to claim 8, further comprising a spacer between the reaction portion and the response unit.

11. The formaldehyde detecting sensor according to claim 1, wherein the hydroxylamine salt is modified by a particle having a particle diameter in a range of 0.05 μm or more and 5000 μm or less.

12. The formaldehyde detecting sensor according to claim 11, wherein the particle is formed of a material selected from the group consisting of polystyrene (PS), polymethyl methacrylate (PMMA), polyacrylamide (PAM), polyethylene terephthalate (PET), polycaprolactone, polyvinyl acetate, polyvinyl ethyl acetate, carbon, glass, and silica.

13. The formaldehyde detecting sensor according to claim 1, wherein the reaction portion further contains a salt of a volatile acid selected from the group consisting of salts of hydrochloric acid, nitric acid, carbonic acid, perchloric acid, and trifluoroacetic acid.

14. The formaldehyde detecting sensor according to claim 1, wherein the hydroxylamine salt and the carbon material are physically spaced apart from each other by a distance in a range of from 0.05 micrometers (μm) to 5000 μm.

* * * * *